United States Patent
Barrelle et al.

(10) Patent No.: US 7,582,073 B2
(45) Date of Patent: *Sep. 1, 2009

(54) SAFETY SHIELD SYSTEM FOR PREFILLED SYRINGE

(75) Inventors: Laurent Barrelle, Saint Nizier du Moucherotte (FR); Lionel Vedrine, Ridgewood, NJ (US); Paul G. Alchas, Franklin Lakes, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 53 days.

This patent is subject to a terminal disclaimer.

(21) Appl. No.: 12/098,770

(22) Filed: Apr. 7, 2008

(65) Prior Publication Data

US 2008/0183137 A1    Jul. 31, 2008

Related U.S. Application Data

(63) Continuation of application No. 10/737,627, filed on Dec. 16, 2003, now Pat. No. 7,455,661, which is a continuation-in-part of application No. 09/838,032, filed on Apr. 19, 2001, now Pat. No. 6,719,730, which is a continuation-in-part of application No. 09/290,786, filed on Apr. 12, 1999, now Pat. No. 6,319,233.

(60) Provisional application No. 60/082,221, filed on Apr. 17, 1998.

(51) Int. Cl.
  *A61M 5/32* (2006.01)

(52) U.S. Cl. .................. 604/192; 604/198; 604/187; 604/110; 604/181

(58) Field of Classification Search ................ 604/187, 604/192, 40, 43, 193, 194, 198, 110, 263, 604/195
See application file for complete search history.

(56) References Cited

U.S. PATENT DOCUMENTS 5,201,708 A * 4/1993 Martin ................. 604/110
5,342,320 A * 8/1994 Cameron ............... 604/192
5,389,085 A * 2/1995 D'Alessio et al. ........ 604/198

* cited by examiner

*Primary Examiner*—Kevin C Sirmons
*Assistant Examiner*—Phillip Gray
(74) *Attorney, Agent, or Firm*—Robert E. West

(57) ABSTRACT

A medical device is provided which includes a shield system and a syringe which is coupled to the shield system. The shield system includes a syringe holder and a shield which is slidably coupled to the holder. A spring resiliently urges the shield from a retracted position to an extended position. Stop members are provided on the holder and shield for maintaining the shield in the retracted position. The syringe is slidably coupled to the holder, and extends within the shield. Axial movement of the syringe with respect to the holder causes disengagement of the stop members, allowing the spring to move the shield to the extended position. Detents are provided on the holder for maintaining the shield in the extended position.

18 Claims, 22 Drawing Sheets

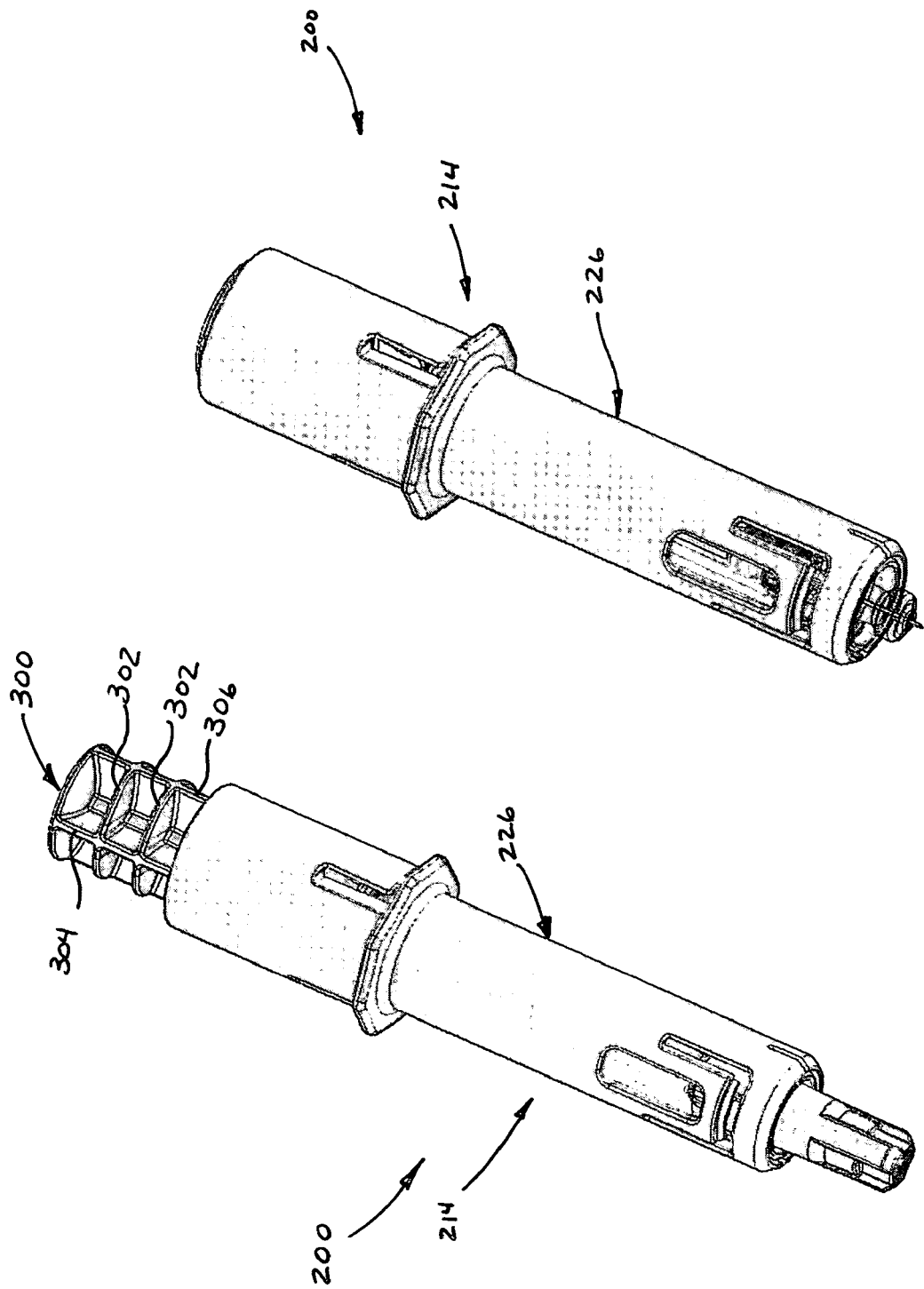

SAFETY SHIELD SYSTEM FOR PREFILLED SYRINGE

CROSS-REFERENCE TO RELATED APPLICATIONS

This patent application is a continuation of U.S. patent application Ser. No. 10/737,627 filed Dec. 16, 2003, currently allowed, which is a continuation-in-part of U.S. patent application Ser. No. 09/838,032, filed on Apr. 19, 2001, now U.S. Pat. No. 6,719,730, which is a continuation-in-part of U.S. patent application Ser. No. 09/290,786 filed on Apr. 12, 1999, now U.S. Pat. No. 6,319,233, which claims priority from U.S. Provisional Patent Application 60/082,221, filed on Apr. 17, 1998.

BACKGROUND OF THE INVENTION

The field of the invention relates to shield systems for protecting against accidental needle stick injury.

Syringes are well known medical devices for administering medicaments to patients. Prefilled syringes are generally considered as those which are filled with a selected dosage of medicament by a pharmaceutical manufacturer for distribution to the end user. They are often comprised of a glass or plastic barrel which contains the medicament and a piston slidably mounted within the barrel. One end of the barrel includes a needle or the like affixed thereto or a connector for a needle assembly such as a Luer fitting. The other end of the syringe is open to allow the insertion of a plunger rod. The plunger rod allows the user to apply manual force to the piston, causing the medicament to be delivered through the needle or other piercing element.

The use of a sharp-pointed piercing element entails the risk of accidental needle stick. To avoid such accidents, many prior art hypodermic syringes have included rigid cylindrical safety shields telescoped over the syringe barrel. These shields can be moved between retracted positions where the needles are exposed for use, to extended positions where the needles are surrounded by the shields. U.S. Pat. Nos. 4,425,120, 4,573,976, 4,850,994 and 4,923,447 disclose various shield systems for hypodermic syringes. The latter two patents disclose shields which are spring-actuated. It is ordinarily desirable to lock the needle shields in the protected positions, and a number of prior art designs provide for such locking. Some systems, such as those disclosed in U.S. Pat. Nos. 5,201,708, 5,242,240 and 5,318,538 are designed to allow the shields to be retracted from their locked, extended positions.

A shield system for protecting the piercing element of a prefilled syringe is disclosed in European Publication No. EP 0 740 942 A1. The disclosed system includes a holder which is coupled to the flange of the syringe barrel, and a shield which is telescopically mounted to the holder. Two hands are required to operate this system.

SUMMARY OF THE INVENTION

The invention relates to a safety shield system for a syringe. In accordance with the preferred embodiments of the present invention, the user is able to cause the shielding of a needle of a syringe by simply applying pressure to the plunger rod of the syringe following injection of the contents of the syringe barrel. The shield may accordingly be deployed automatically through the use of only one hand. As there is no need to place the hand near the needle for any purpose, the risk of needle stick injury is reduced.

In accordance with the objects of the invention, the shield system coupled with a syringe may comprises a medical device. The inventive shield system includes a holder which defines an enclosure. The syringe barrel extends at least partially, and preferably almost entirely, within the enclosure. The barrel is slidable within the holder. A retainer is positioned on the holder, and is engageable with the barrel. The retainer prevents the barrel from being uncoupled from the holder. A shield is mounted to the holder, and positioned about at least a portion of the barrel. The shield is axially movable with respect to the holder between retracted and extended positions. It is intended to cover the needle tip when in the extended position. A spring engages the shield, and urges it towards the extended position. Complementary structure is provided on the shield and holder to releasably retain the shield in the retracted position. Complementary structure is also provided on the shield and holder to lockingly retain the shield in the extended position. A first stop member is positioned on the shield, and a second stop member is positioned on the holder. The second stop member is releasably engageable with the first stop member when the shield is in the retracted position. The force of the spring, by itself, is insufficient to cause disengagement of the first and second stop members. The barrel is operationally coupled to the shield such that sufficient axial movement of the barrel causes disengagement of the first and second stop members. Such movement of the barrel is ordinarily caused by pressure on the plunger rod of the syringe following complete injection of the contents of the barrel. Upon disengagement of the first and second stop members, the spring causes the shield to move to the extended position.

The proximal end of the holder is preferably adapted to engage and retain the flange of the syringe provided at the proximal end of the syringe barrel. The axial movement of the shield is preferably limited by a set of locking detents formed on the holder. The shield is preferably positioned within the holder such that an end of the spring engages a part of the shield, and the opposite end of the spring engages a part of the holder or syringe.

The shield system according to the invention is comprised of a holder, a shield, a spring and an end fitting. The holder is adapted for receiving at least a flanged portion of the barrel of a syringe, and includes axially spaced, opposing abutment surfaces to retain the flange. The distance between these surfaces corresponds to the distance the syringe can be axially moved with respect to the holder once mounted thereto. The shield is slidably mounted to the holder, and is movable between retracted and extended positions. A spring urges the shield towards the extended position. The holder includes a stop member which is engageable with the shield to maintain it in the retracted position. Sufficient axial movement of the shield causes disengagement of the stop member, allowing the spring to move the shield to the extended position. An end fitting is preferably incorporated in the system to maintain the position of the spring prior to insertion of a syringe into the holder.

The shield system facilitates the safe use of prefilled syringes, though it can be adapted for other sharp-pointed medical devices, such as syringes filled just before use, as well. When employed with a syringe, the system allows the contents of the syringe to be expressed in a conventional manner. Continued, and preferably increased pressure on the plunger rod following injection causes the syringe barrel to move axially, thereby axially displacing the shield and causing disengagement of the complementary structure on the shield and holder. Such displacement causes release of the stop member, and the spring to move the shield over the needle of the syringe thus providing protection against needle stick injury.

An embodiment of the present invention is directed to a safety shield system for use with a syringe having a barrel defining a reservoir within which a medicament may be held. The syringe has a needle affixed to the barrel and in fluid communication with the reservoir. The syringe further includes a plunger rod and piston selectively movable within the reservoir along an injection stroke; the medicament being expelled from the reservoir through the needle by movement of the plunger rod and piston in the reservoir. The inventive safety shield system of this embodiment comprises a holder and a retainer defined on the holder and comprising a detent and two confrontingly oppositely disposed surfaces. The retainer non-releasably secures a flange of the syringe barrel within the holder and permits limited axial movement of the barrel therein and with respect thereto. The limited axial movement of the barrel being caused by movement of the plunger rod and piston to or near the end of the injection stroke. The inventive safety shield system further comprises a shield coupled to the holder, the shield being axially movable with respect to the holder from a retracted position, in which a part of the needle is not contained within the shield, and an extended position, in which the needle is contained within the shield. The inventive safety shield system further comprises a spring urging the shield towards the extended position, a first stop member provided on one of the shield and the holder, and a second stop member provided on the other one of the shield and the holder and engageable with the first stop member to releasably hold the shield in the retracted position. The barrel of the syringe is operationally coupled to the shield such that axial movement of the barrel in the direction of the needle at or near the end of the injection stroke causes disengagement of the first and second stop members, allowing the spring to move the shield to the extended position.

Another embodiment of the present invention is directed to a safety shield system for use with a syringe having a barrel defining a reservoir within which a medicament may be held. The syringe has a needle affixed to the barrel and in fluid communication with the reservoir. The syringe further includes a plunger rod and piston selectively movable within the reservoir along an injection stroke; the medicament being expelled from the reservoir through the needle by movement of the plunger rod and piston in the reservoir. The inventive safety shield system of this embodiment comprises a holder and a retainer defined on the holder and comprising a detent and two confrontingly oppositely disposed surfaces. The retainer non-releasably secures a flange of the syringe barrel within the holder and permits limited axial movement of the barrel therein and with respect thereto. The limited axial movement of the barrel being caused by movement of the plunger rod and piston to or near the end of the injection stroke. The inventive safety shield system further comprises a shield coupled to the holder and axially movable with respect to the holder between an extended position, in which the needle is contained within the shield, and a retracted position, in which a part of the needle is not contained within the shield. The inventive safety shield system further comprises a spring urging the shield towards the extended position, a detent defined on the holder, and a rib defined on the shield and engageable with the detent to secure the shield in the extended position. The shield is initially deployed in the extended position and is movable from the extended position to the retracted position upon contact with the skin of a patient, the spring urging the shield from the retracted position to the extended position upon removal of contact with the skin of the patient, the detent and rib lockingly securing the shield in the extended position.

Yet another embodiment of the present invention is directed to a medical device comprising a syringe coupled to a safety shield system. The syringe comprises a barrel defining a reservoir within which a medicament may be held, a hub defined at an end of the barrel and defining a generally flat skin engaging surface, a needle having a forward tip and being affixed to the barrel and in fluid communication with the reservoir, the forward tip of the needle extending beyond the skin engaging surface a distance ranging from 0.5 mm to 3 mm, and a plunger rod having a piston secured thereto. The piston is selectively movable within the reservoir along an injection stroke with the medicament being expelled from the reservoir through the needle by movement of the piston in the reservoir along the injection stroke.

The safety shield system of this embodiment comprises a holder and a retainer defined on the holder and comprising a detent and two confrontingly oppositely disposed surfaces. The retainer non-releasably secures a flange of the syringe barrel within the holder and permits limited axial movement of the barrel therein and with respect thereto. The limited axial movement of the barrel being caused by movement of the plunger rod and piston to or near the end of the injection stroke. The inventive safety shield system further comprises a shield coupled to the holder, the shield being axially movable with respect to the holder from a retracted position, in which a part of the needle is not contained within the shield, and an extended position, in which the needle is contained within the shield. The inventive safety shield system further comprises a spring urging the shield towards the extended position, a first stop member provided on one of the shield and the holder, and a second stop member provided on the other one of the shield and the holder and engageable with the first stop member to releasably hold the shield in the retracted position. The barrel of the syringe is operationally coupled to the shield such that axial movement of the barrel in the direction of the needle at or near the end of the injection stroke causes disengagement of the first and second stop members, allowing the spring to move the shield to the extended position.

Yet another embodiment of the present invention is directed to a medical device comprising a syringe coupled to a safety shield system. The syringe comprises a barrel defining a reservoir within which a medicament may be held, a hub defined at an end of the barrel and defining a generally flat skin engaging surface, a needle having a forward tip and being affixed to the barrel and in fluid communication with the reservoir, the forward tip of the needle extending beyond the skin engaging surface a distance ranging from 0.5 mm to 3 mm, and a plunger rod having a piston secured thereto. The piston is selectively movable within the reservoir along an injection stroke with the medicament being expelled from the reservoir through the needle by movement of the piston in the reservoir along the injection stroke.

The inventive safety shield system of this embodiment comprises a holder and a retainer defined on the holder and comprising a detent and two confrontingly oppositely disposed surfaces. The retainer non-releasably secures a flange of the syringe barrel within the holder and permits limited axial movement of the barrel therein and with respect thereto. The limited axial movement of the barrel being caused by movement of the plunger rod and piston to or near the end of the injection stroke. The inventive safety shield system further comprises a shield coupled to the holder and axially movable with respect to the holder between an extended position, in which the needle is contained within the shield, and a retracted position, in which a part of the needle is not contained within the shield. The inventive safety shield system further comprises a spring urging the shield towards the extended position, a detent defined on the holder, and a rib defined on the shield and engageable with the detent to secure the shield in the extended position. The shield is initially deployed in the extended position and is movable from the extended position to the retracted position upon contact with the skin of a patient, the spring urging the shield from the retracted position to the extended position upon removal of contact with the skin of the patient, the detent and rib lockingly securing the shield in the extended position.

BRIEF DESCRIPTION OF THE DRAWINGS

FIGS. 20a-b are perspective views of an alternate embodiment of a medical device according to the present invention;

DETAILED DESCRIPTION OF THE INVENTION

Figure 1:
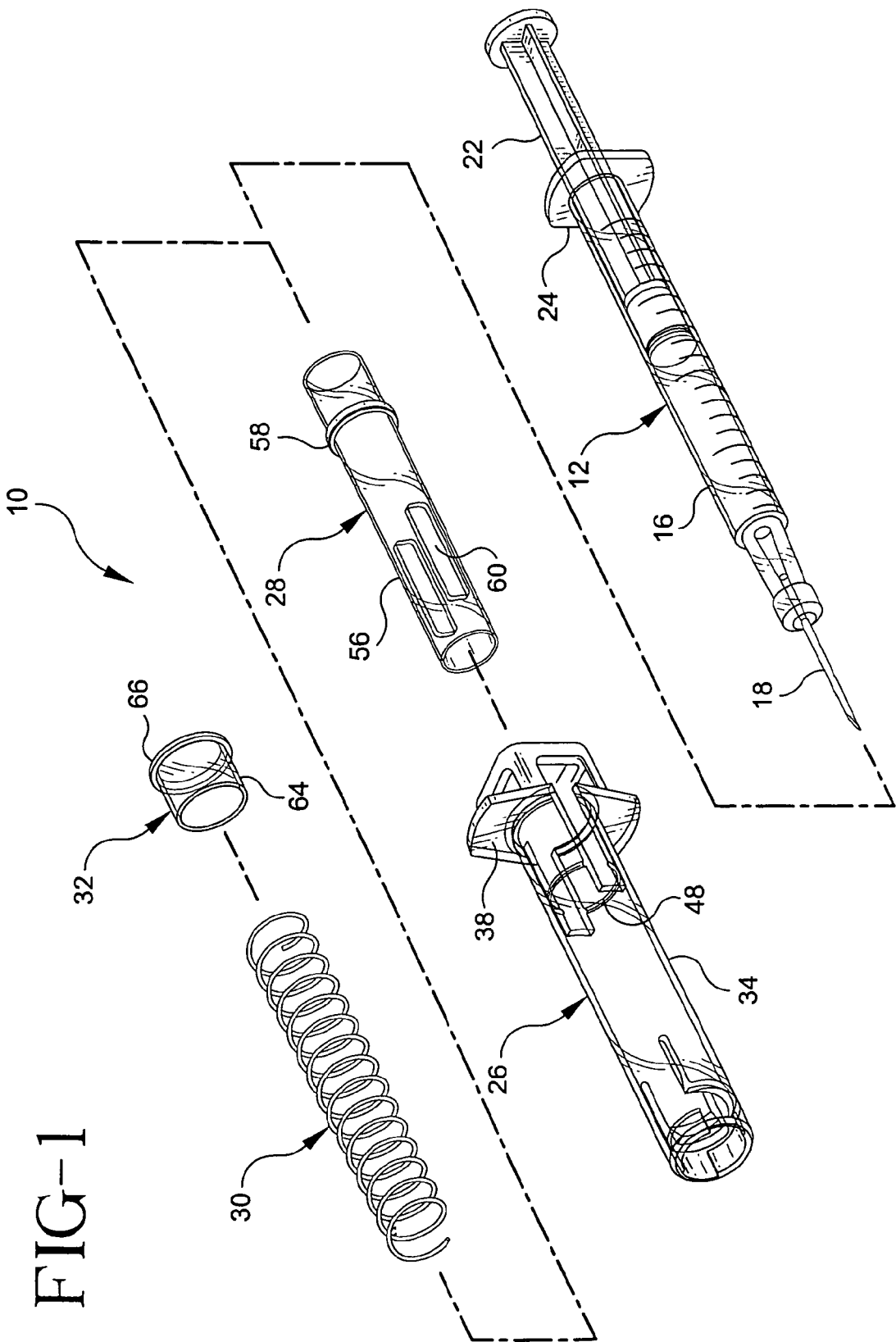
FIG. 1 is an exploded, perspective view showing a medical device according to a first embodiment of the invention.
Figure 2:
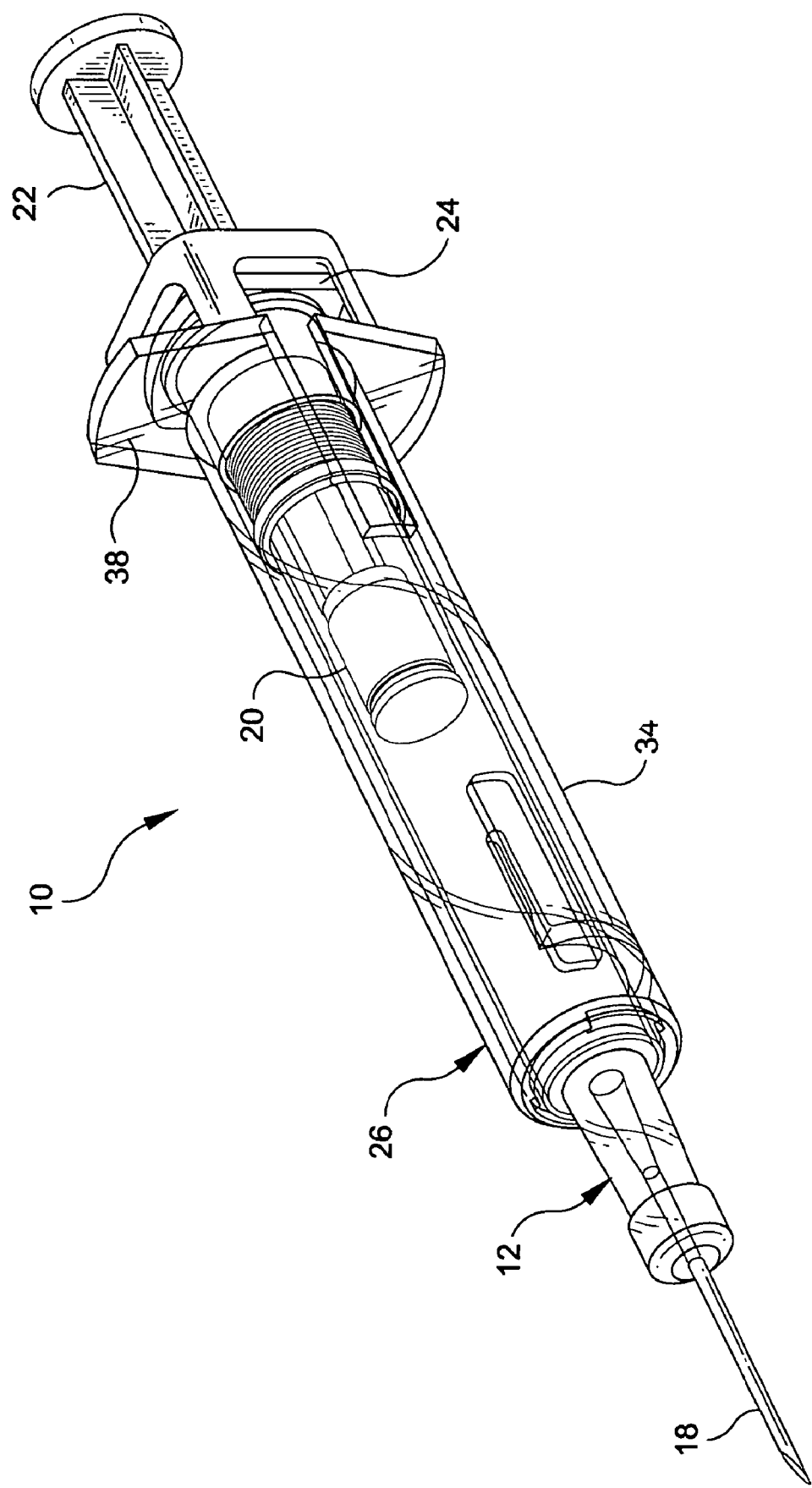
FIG. 2 is a top perspective view of the medical device as assembled.

A first embodiment of a safety shield system 14 coupled together with a syringe 12 and comprising a medical device 10 for injecting a medicament into a patient is shown in FIGS. 1-11.

Syringes are ordinarily comprised of a generally cylindrical portion, known as a barrel, a needle or other piercing or connecting element secured to one end of the barrel, and a piston or stopper slidably positioned within the barrel. The needle may be removably secured to the barrel, but is more likely to be permanently secured to the barrel when the barrel is comprised of glass. Glass barrels are commonly used in prefillable syringes, and ordinarily contain a single dose of medication. Prefilled syringes made from plastic are also known to the art. The shield system 14 disclosed herein is employed in conjunction with a prefillable syringe including a barrel 16, a cannula such as a needle 18 permanently secured to the barrel, a piston 20 slidably positioned with the barrel, and a plunger rod 22 engageable with the piston. The syringe barrel 16 includes a radially outwardly extending flange 24, which is used to couple the syringe 12 to the shield system 14.

The shield system 14 according to the invention includes a holder 26, a shield 28 coupled to the holder, and a spring 30. It also preferably includes a holder end fitting 32 which engages one end of the spring. With the exception of the spring 30, all of the components of the system are made from a semi-rigid plastic material such as polypropylene. The spring 30 is preferably a metal coil spring.

The holder 26 is preferably comprised of an elongate, generally cylindrical body 34 which defines a generally cylindrical enclosure 36. The holder has first and second open ends which provide access to the enclosure. A flange 38 extends radially outwardly from the holder body near the second open end thereof. The flange 38 and body 34 of the holder 26 are designed for simple, one-handed use in making an injection.

The inner surface of the holder includes a frustoconical portion 40 adjoining the second open end. A first abutment surface 42 is formed at the inner end of this surface. A second abutment surface 44 is formed by the holder body in opposing relation to the first abutment surface. As described below, the axial spacing between these surfaces corresponds, though is not equal to the axial distance which the syringe can move with respect to the holder. The inner diameter of the holder, measured at the abutment surfaces, is smaller than the distance between the edges of the syringe flange 24. Accordingly, once the syringe is inserted far enough into the holder that the flange 24 is between abutment surfaces 42, 44, it is slidably coupled to the holder. The spring 30 urges the syringe flange into engagement with the first abutment surface 42.

One or more openings, such as openings 46A, 46B, are formed in the holder body. These openings are in opposing relation, and about ninety degrees offset from the axis including the maximum dimension of the holder flange 38. The openings extend between the first abutment surface 42 and a point nearly half way to the first open end of the holder. The sizes of the openings are selected based upon the amount of flexibility desired in the holder body. Flexibility of the holder body or shield may also be provided by virtue of the materials which comprise these elements and the wall thicknesses thereof. Each includes a relatively wide portion between the first abutment surface 42 and the flange 38.

A generally annular stop member 48 is provided on the holder in the form of an inwardly extending protrusion. Alternatively, a series of discrete protrusions (not shown) may be employed. The stop member is interrupted by the openings 46A, 46B, and includes an inclined surface facing the second open end of the holder body.

Figure 12B:
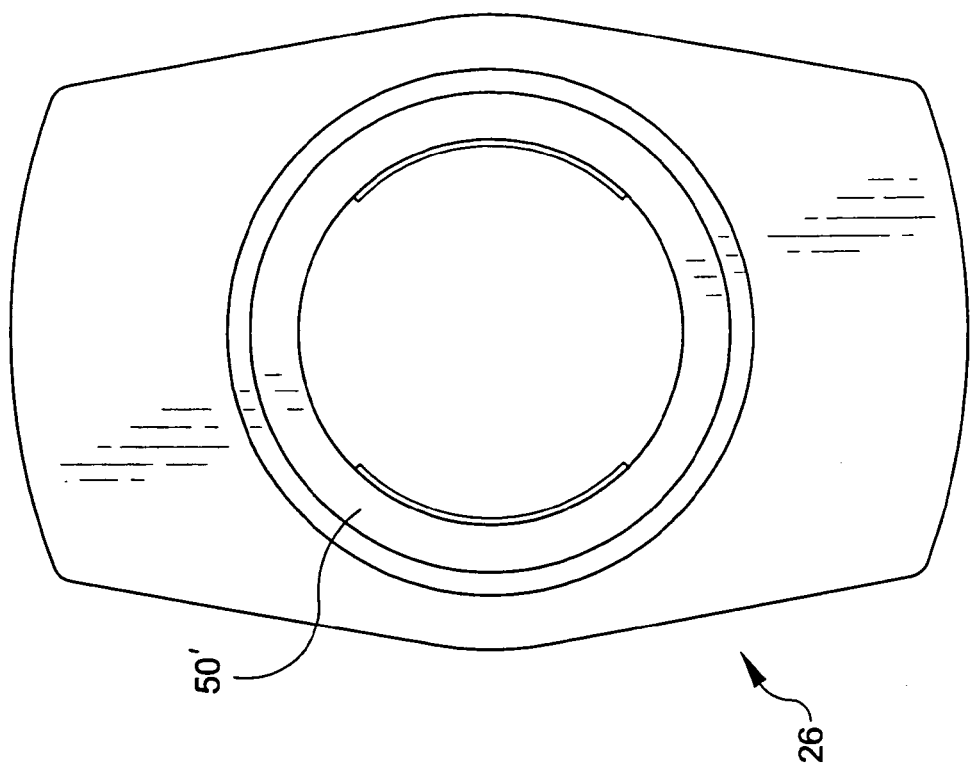
FIG. 12B is an end view of an alternative embodiment of the syringe holder.
Figure 12A:
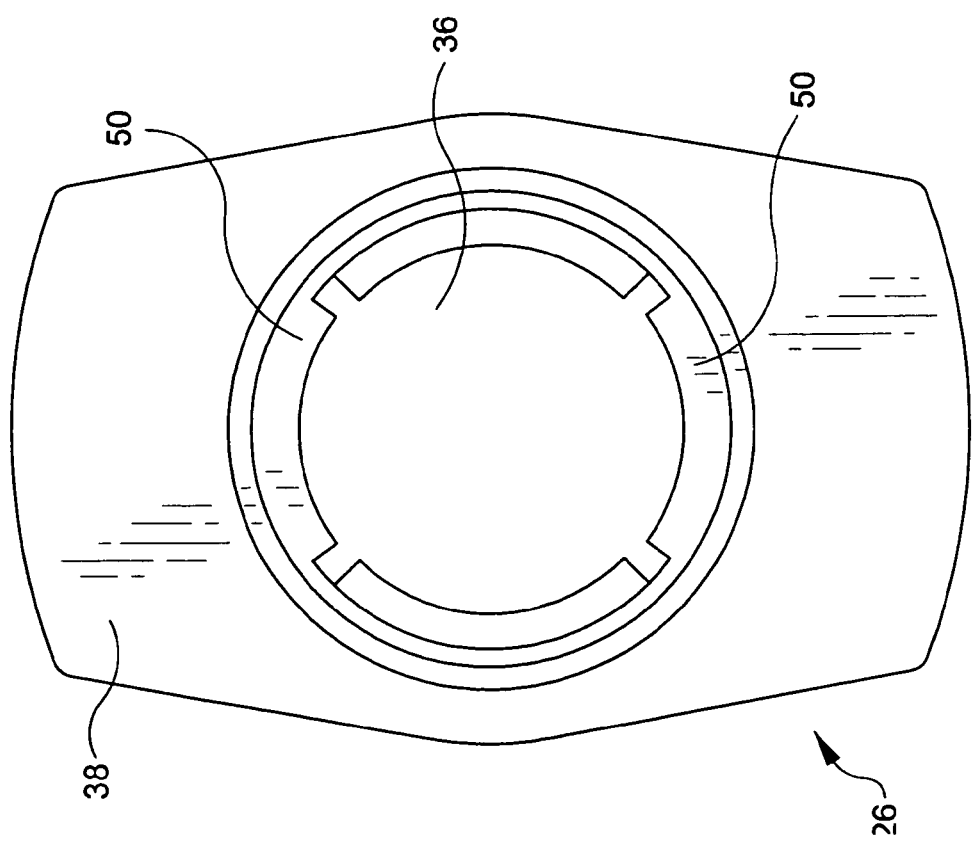
FIG. 12A is an end view of the syringe holder of the device.

A pair of first detents 50 are provided at or near the first open end of the holder. Each first detent is in the form of a projection extending radially inwardly from the body of the holder. As shown, in FIG. 12A, the first detents 50 are in opposing relation. Alternatively, a single, continuous detent in the form of an annular collar 50 may be provided, as shown in FIG. 12 B.

A second pair of detents 52 are provided on the holder, and are axially spaced from the first detents. Each of these detents 52 is formed on an axially extending arm 54 which is integral with the holder body 34 and pivotable with respect thereto. The end surface of each detent facing the first open end of the holder is substantially perpendicular to the longitudinal axis of the holder. An inclined end surface is provided on the opposite side of each detent, and faces the second open end.

The shield 28 is comprised of a substantially cylindrical body 56. It is preferably small enough in diameter to be positioned within the holder, and large enough to fit over the barrel 16 of the syringe. A stop member 58 in the form of a radially outwardly extending collar is formed on the body 56 of the shield. This stop member has an inclined surface which is engageable with the inclined surface of the stop member 48 on the holder. Axially extending ribs 62 may be provided on the interior surface of the body for engaging a syringe barrel. Openings 60 in the shield provide flexibility for the shield body. The resilient engagement of the syringe barrel by the ribs allows the shield to slide with respect to the barrel without excess lateral play between the barrel and shield.

The spring 30 is sized to fit over the shield such that one end thereof bears against the shield stop member 58. The opposite end of the spring bears against the end fitting 32 of the syringe flange 24.

The spring may be used to cause the shield to move axially upon axial movement of the syringe barrel if it is fully compressed when the shield is in the retracted position. Direct engagement of the syringe flange 24 and shield, as provided in the preferred embodiment, would be unnecessary in such an arrangement. The operation of the device can be effected whether the shield, spring, end fitting and syringe barrel are directly or indirectly engaged, so long as axial movement of the syringe barrel causes axial movement of the shield. As discussed below, the use of an end fitting is optional.

The end fitting 32 includes a cylindrical body 64 which can be inserted within the body 34 of the holder. One end of the spring 30 is insertable within the end fitting. An annular wall 66 is provided at one end of the cylindrical body 64, and is preferably integral therewith. This wall extends radially outwardly and radially inwardly with respect to the cylindrical body 64. The radially outwardly extending portion of the wall is adapted to engage the first abutment surface 42, so that it can be snapped behind the frustoconical portion at the second open end of the holder. It is used to maintain the spring 30 in position within the holder, thereby allowing the shield system to be manufactured as an assembly which does not include the syringe. The radially inwardly extending portion of the wall is adapted to engage between the first end of the spring 30 and the syringe flange 24. It will accordingly protect this flange from direct contact with the spring. Such protection is desirable where the shield system is used in conjunction with a glass syringe in order to prevent breakage. In the absence of the optional end fitting 32, the first abutment surface 42 will function to retain the syringe within the holder by engaging the syringe flange directly. The particular structure of the retainer or retainers is unimportant so long as the syringe remains slidably coupled to the holder during use of the device. Axial movement of the syringe causes corresponding axial movement of the end fitting until the inwardly extending portion of the annular wall 66 engages the first end of the shield 28. In the absence of the end fitting, the syringe flange 24 would engage this surface directly.

Figure 13:
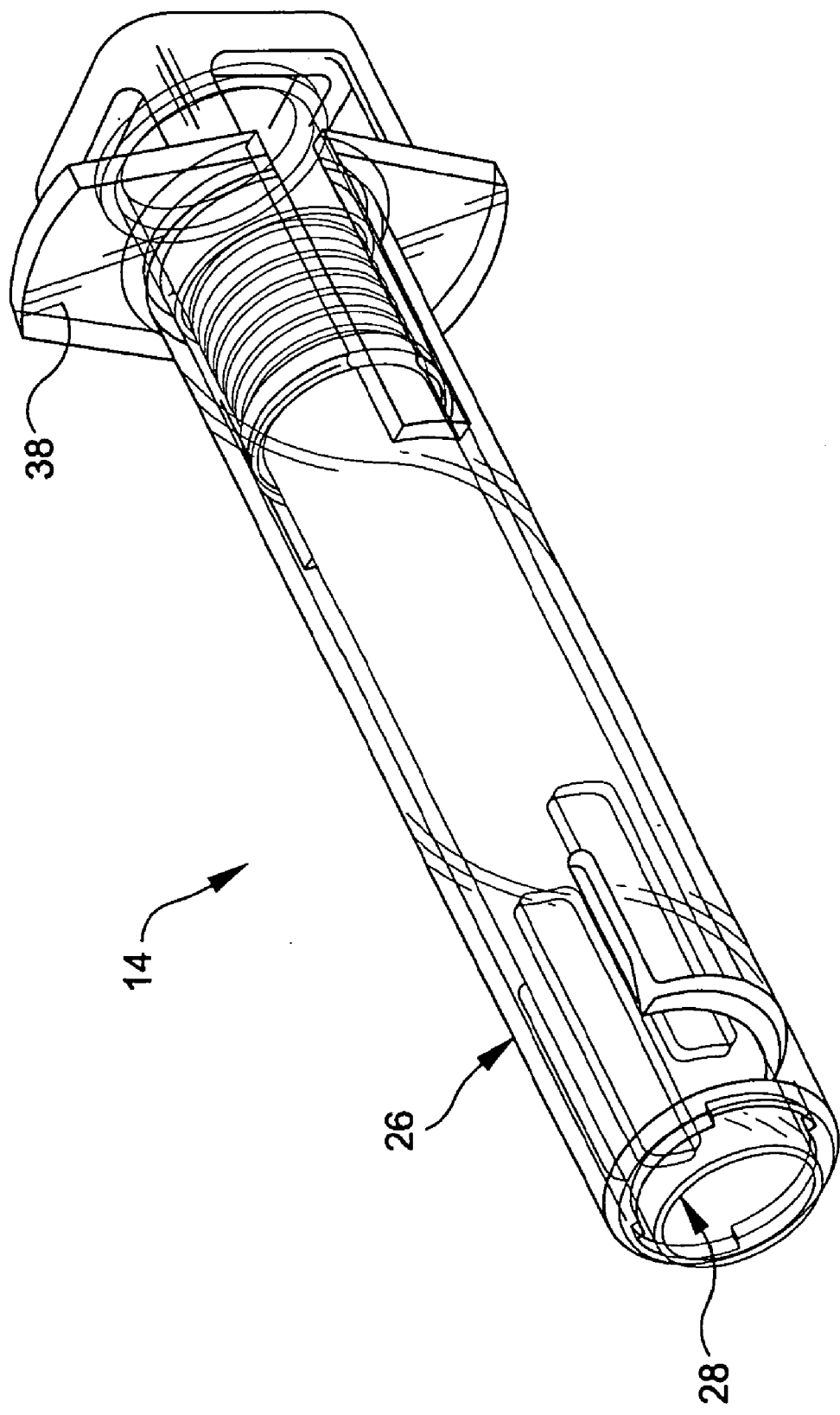
FIG. 13 is a perspective view of the shield system employed in the medical device shown in FIGS. 1-12.

The assembly and use of this preferred embodiment of the invention shall now be described. The shield 28 is slidably mounted to the holder by inserting it through the second open end thereof. The engagement of the stop members 48, 58 limits such insertion. The spring is inserted through the second open end of the holder, and over the shield until it abuts the shield stop member 58. As a final step prior to providing the shield system to the end user, the end fitting 32 is slipped over the exposed end of the spring and pushed through the second open end of the holder. The spring is substantially compressed during this step. The shield is resiliently urged towards the first open end of the holder while the end fitting is urged towards the second open end thereof. Neither element can move due to the engagement of the stop members 48, 58, and the annular wall 66 with the first abutment surface 42, respectively. The force of the spring 30 is insufficient to cause the disengagement of these members. The shield system may be provided to end users or pharmaceutical manufacturers in the form shown in FIG. 13.

The shield system 14 receives a syringe of appropriate size through the second open end of the holder. The system as shown is designed for receiving a syringe including a flange. The syringe is inserted into the shield until the flange 24 snaps behind the first abutment surface 42. The end fitting 32 is displaced slightly during this procedure. As the needle of the syringe is ordinarily protected by a cover at this time, it may be safely coupled to the shield system.

The force required to disengage the stop members 48,58 should be greater than the force required to expel the contents of the syringe barrel. The plunger rod is employed to move the piston 20 down the syringe barrel until the contents of the barrel have been completely expelled. (The cover is, of course, removed prior to injection.) The contents of the barrel of a prefillable syringe ordinarily correspond to a single dose of the prescribed medicament.

Following removal of the needle 18 from the patient, the user applies a greater force to the plunger rod than that applied during injection. Such force causes axial displacement of the end fitting, the spring and the shield with respect to the holder. The distance between the annular wall 66 of the end fitting (or the flange 24) and the second abutment surface 44 is sufficient to allow the second stop member 58 to move far enough axially to where its retention by the first stop member 48 is overcome by the force of the spring. In the preferred embodiment, this is accomplished as the inclined surfaces of the stop members slide past each other. The first stop member 48 is also displaced radially as such sliding occurs due to the flexibility of the holder body portion which adjoins it.

Figure 4:
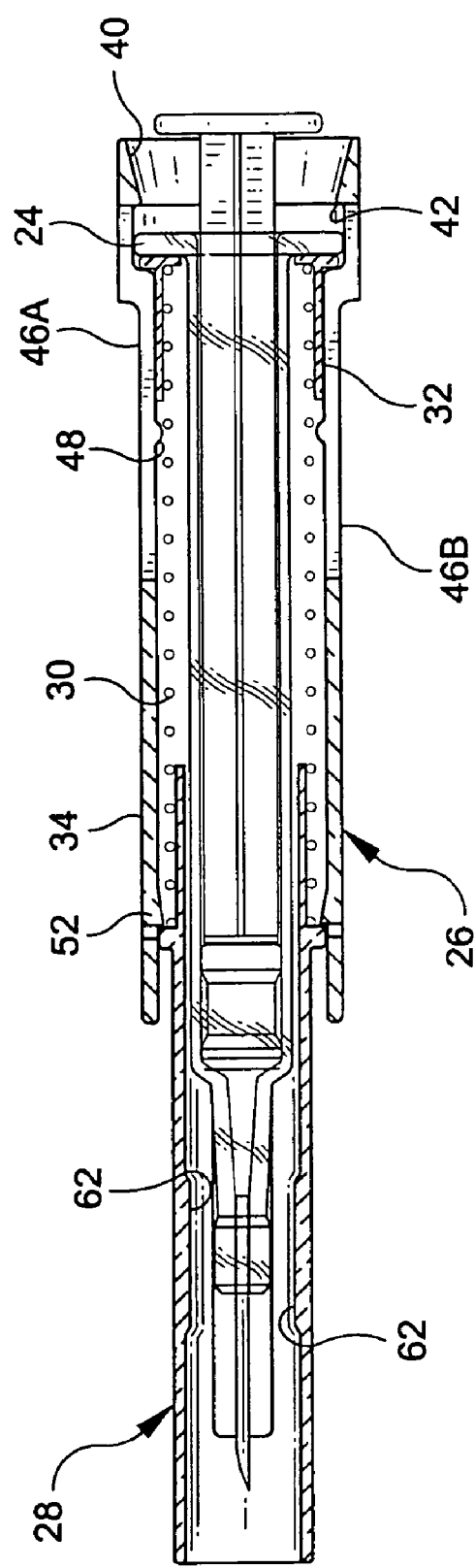
FIG. 4 is a sectional view thereof following actuation of the shield system of the device.
Figure 5:
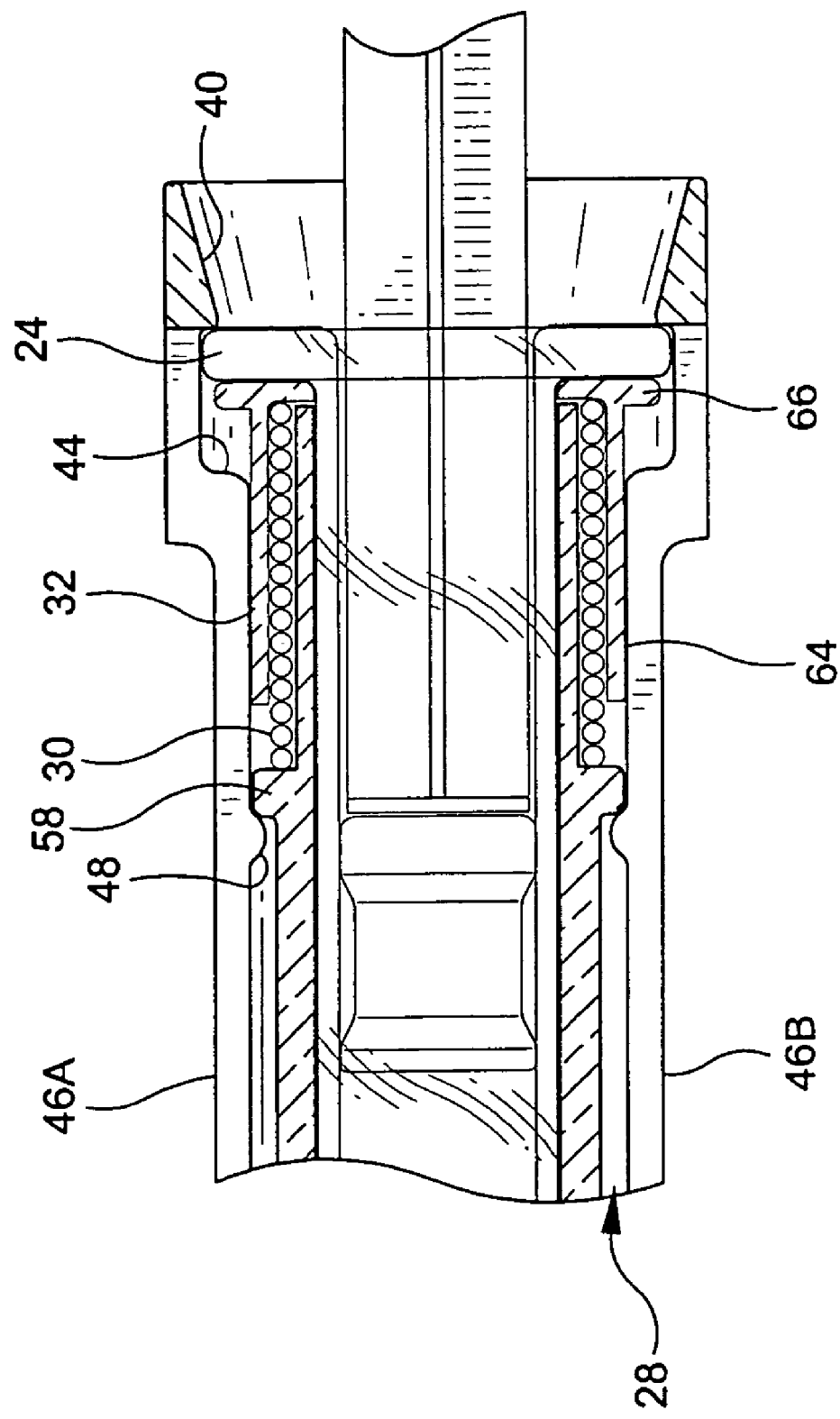
FIG. 5 is an enlarged sectional view of the proximal portion of the device prior to actuation of the shield system.
Figure 6:
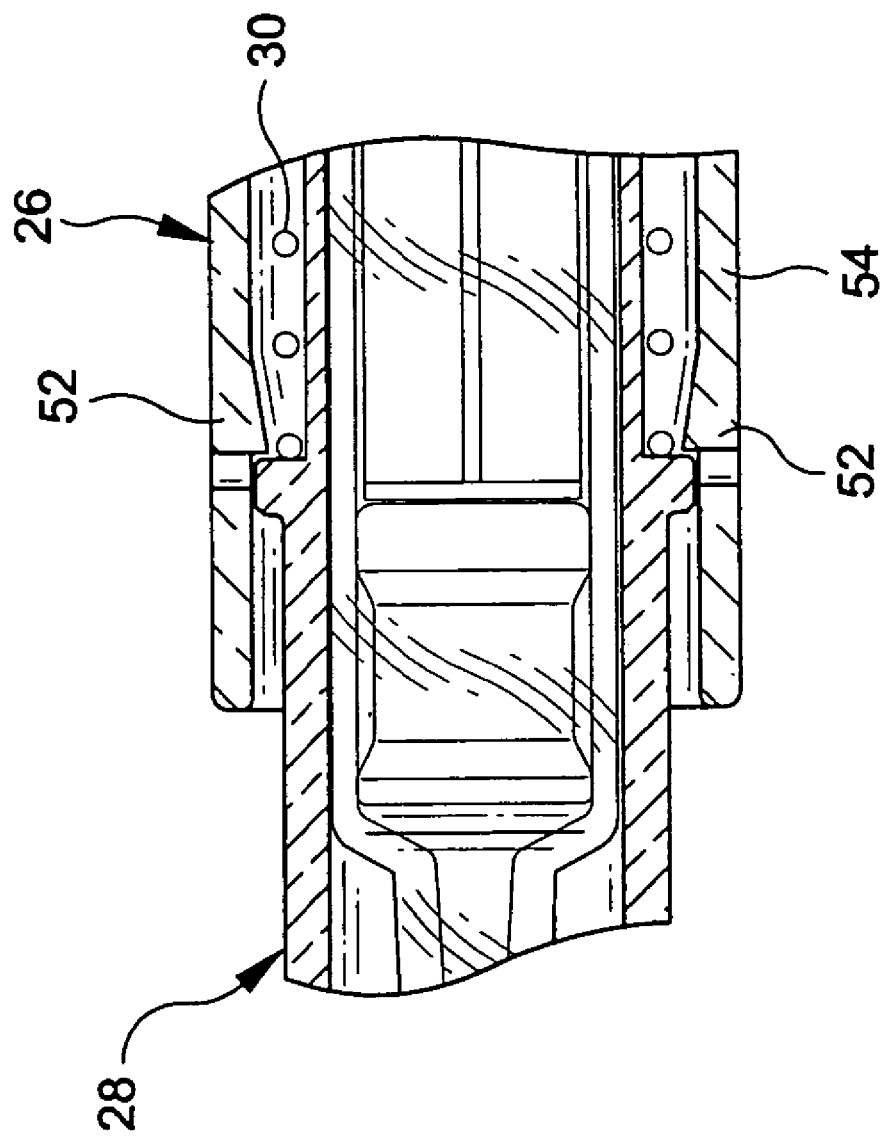
FIG. 6 is an enlarged sectional view showing a portion of the device, including the distal portion of a syringe holder of the device, following actuation of the shield system.
Figure 7:
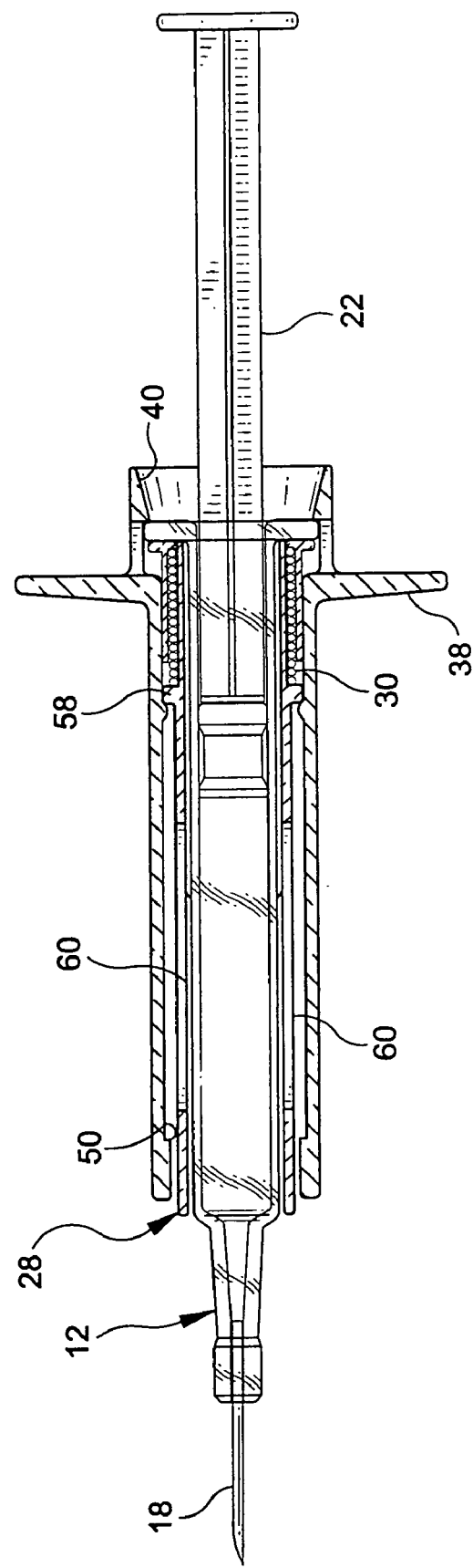
FIG. 7 is a sectional elevation view of the device rotated ninety degrees from the view provided in FIG. 3.
Figure 8:
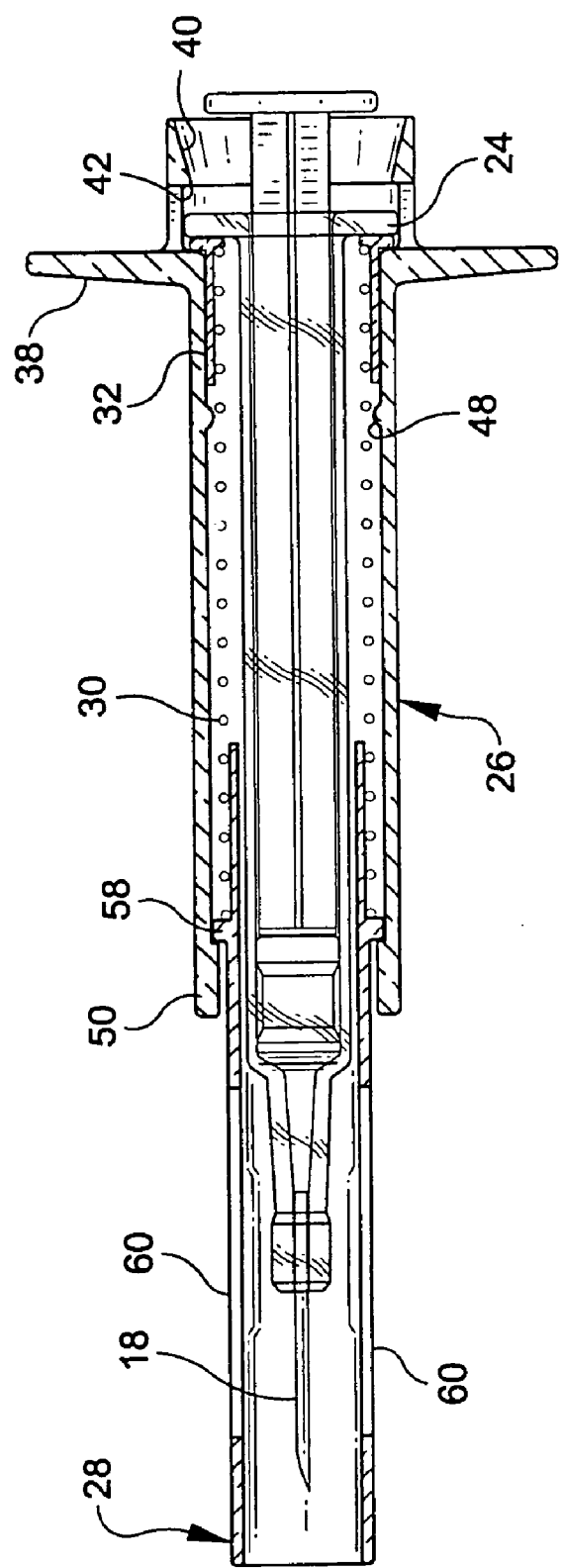
FIG. 8 is a sectional elevation view of the device following actuation of the shield system rotated ninety degrees from the view provided in FIG. 4.
Figure 9:
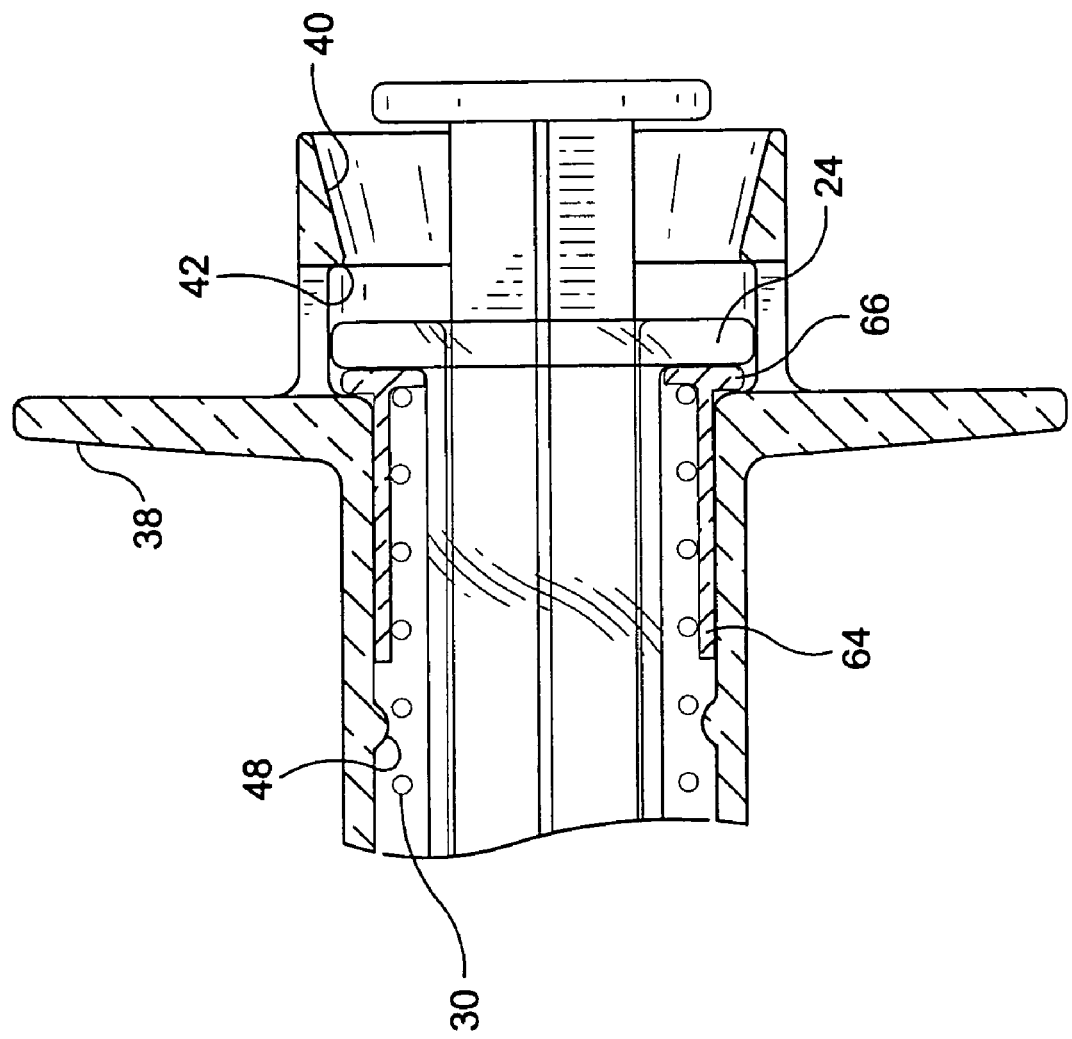
FIG. 9 is an enlarged sectional view of the proximal end portion of the device following actuation of the shield system.
Figure 10:
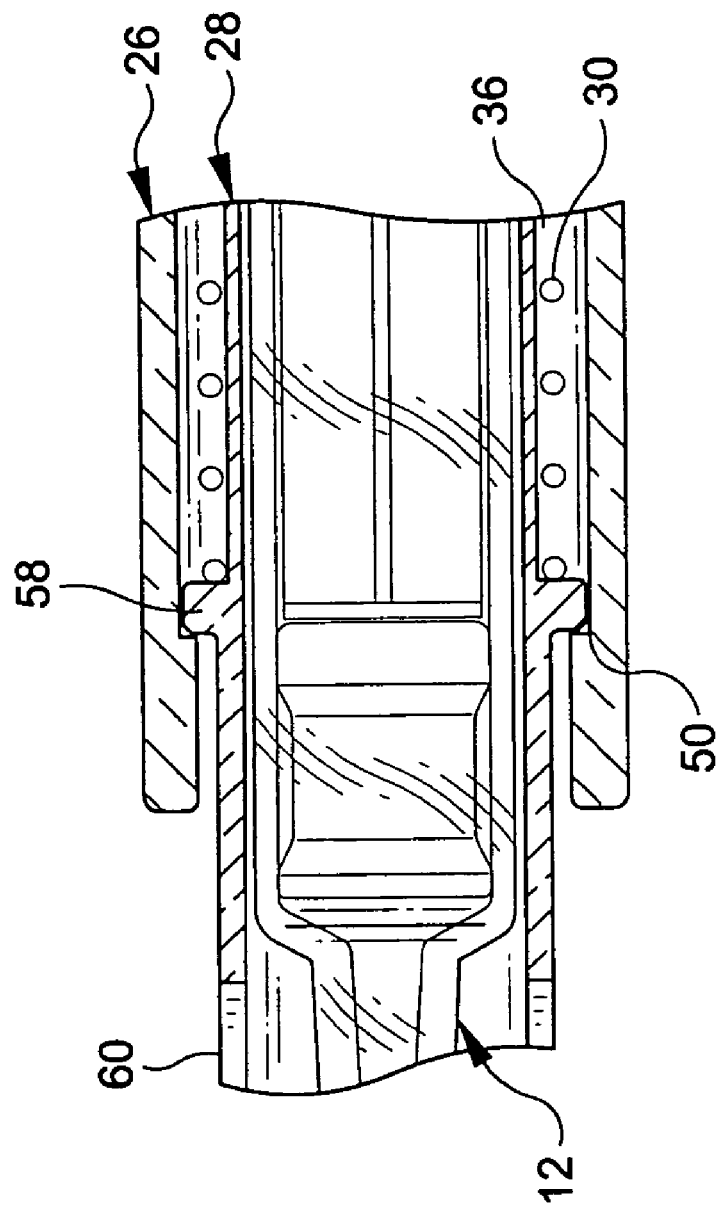
FIG. 10 is an enlarged sectional view similar to that shown in FIG. 6, but rotated ninety degrees with respect thereto.
Figure 11:
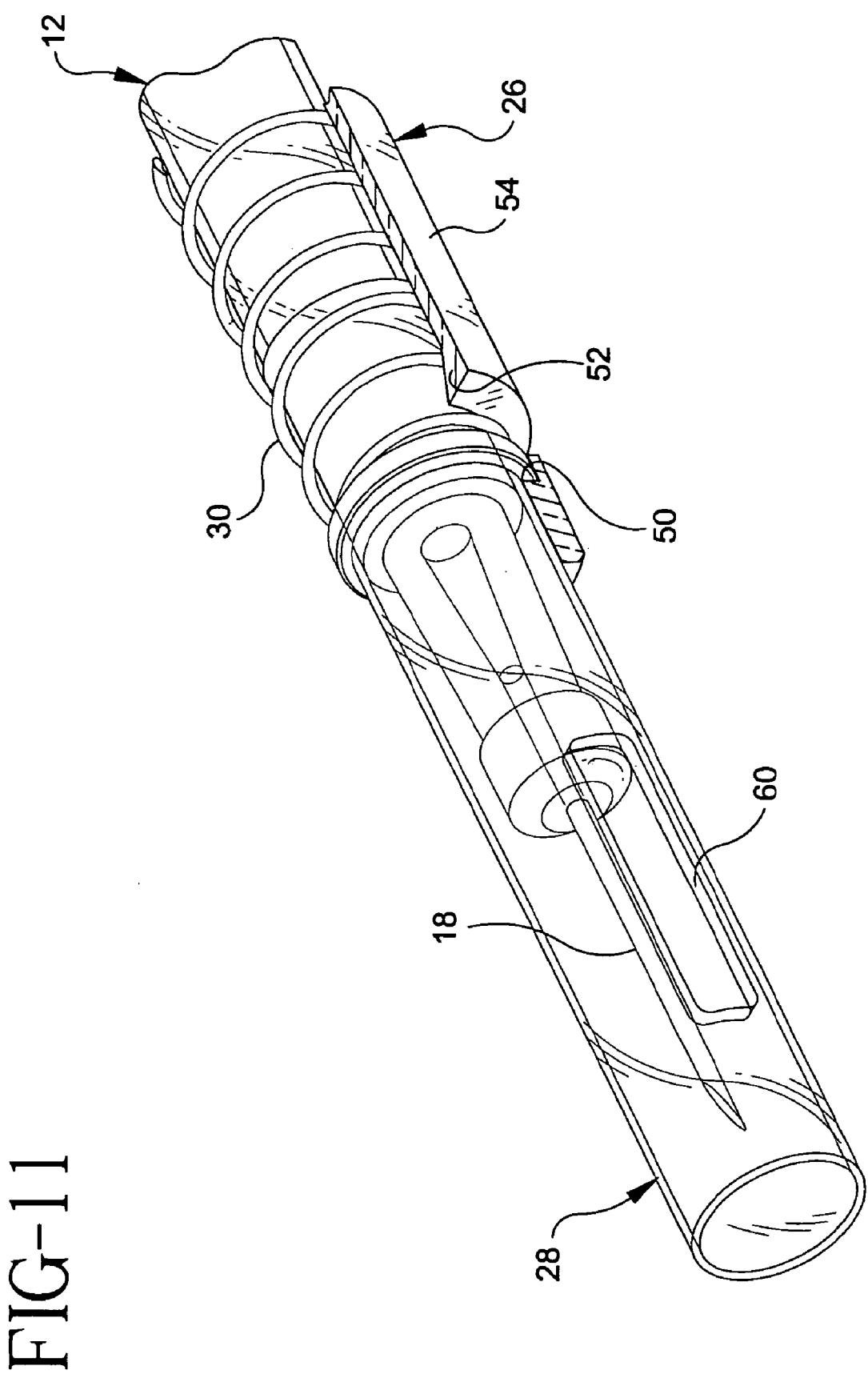
FIG. 11 is enlarged, partially cut-away perspective view showing the distal end of the device following actuation of the shield system.

Once the stop members 48, 58 are disengaged, the spring 30 expands rapidly, causing the shield to slide axially with respect to the holder and syringe barrel. The stop member 58 moves past the second detents 52, causing them to deflect radially outwardly and then inwardly to their original positions. It finally engages the first detents 50. Upon such engagement, the needle 18 is entirely and permanently covered by the shield, as shown in FIGS. 4 and 8. The shield cannot be retracted sufficiently to expose the needle tip due to the engagement of the stop member 58 with the second detents. It cannot be removed from the holder as the stop member 58 cannot move past the first detents 50.

The above-described procedure is particularly safe as it can be accomplished using only one hand. No second hand is required to push a button or use any other actuating member to release the spring. The risk of accidental actuation of the shield through inadvertent contact with an actuating button is eliminated. Moreover, a one-handed system is simpler for most people to use. It is readily apparent that the shield system can be adapted for use with syringes of various shapes and sizes without major modification.

The deployment of a shield in response to the axial displacement of a syringe barrel with respect to a holder is a safe and effective way of protecting against needle sticks. The preferred embodiment of the invention, as described above, provides advantages for the user as well as the manufacturer. The components are relatively easy to manufacture and assemble. It will be appreciated, however, that modifications can be made without changing the basic mode of operation of the device.

A second embodiment of the invention is shown in FIGS. 14-19. It is less preferred than the embodiment shown in FIGS. 1-11, but is still effective in providing the shielding of a needle or other like sharp-pointed instrument in response to the axial movement of the instrument. No end fitting is employed in this embodiment of the invention. The spring is instead held in position directly by the flange 24 of the syringe.

Figure 14:
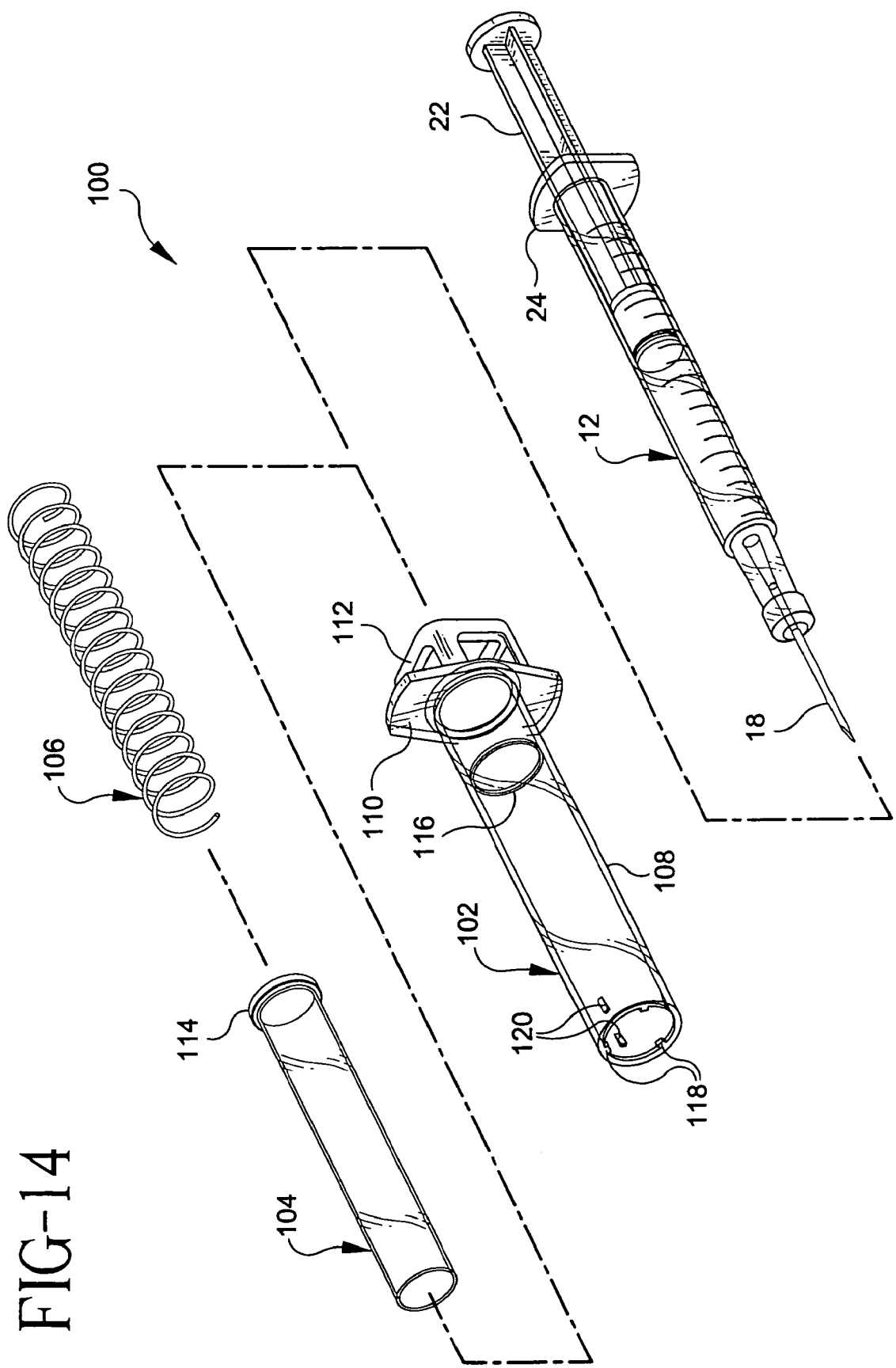
FIG. 14 is an exploded, perspective view showing a medical device according to a second embodiment of the invention.
Figure 15:
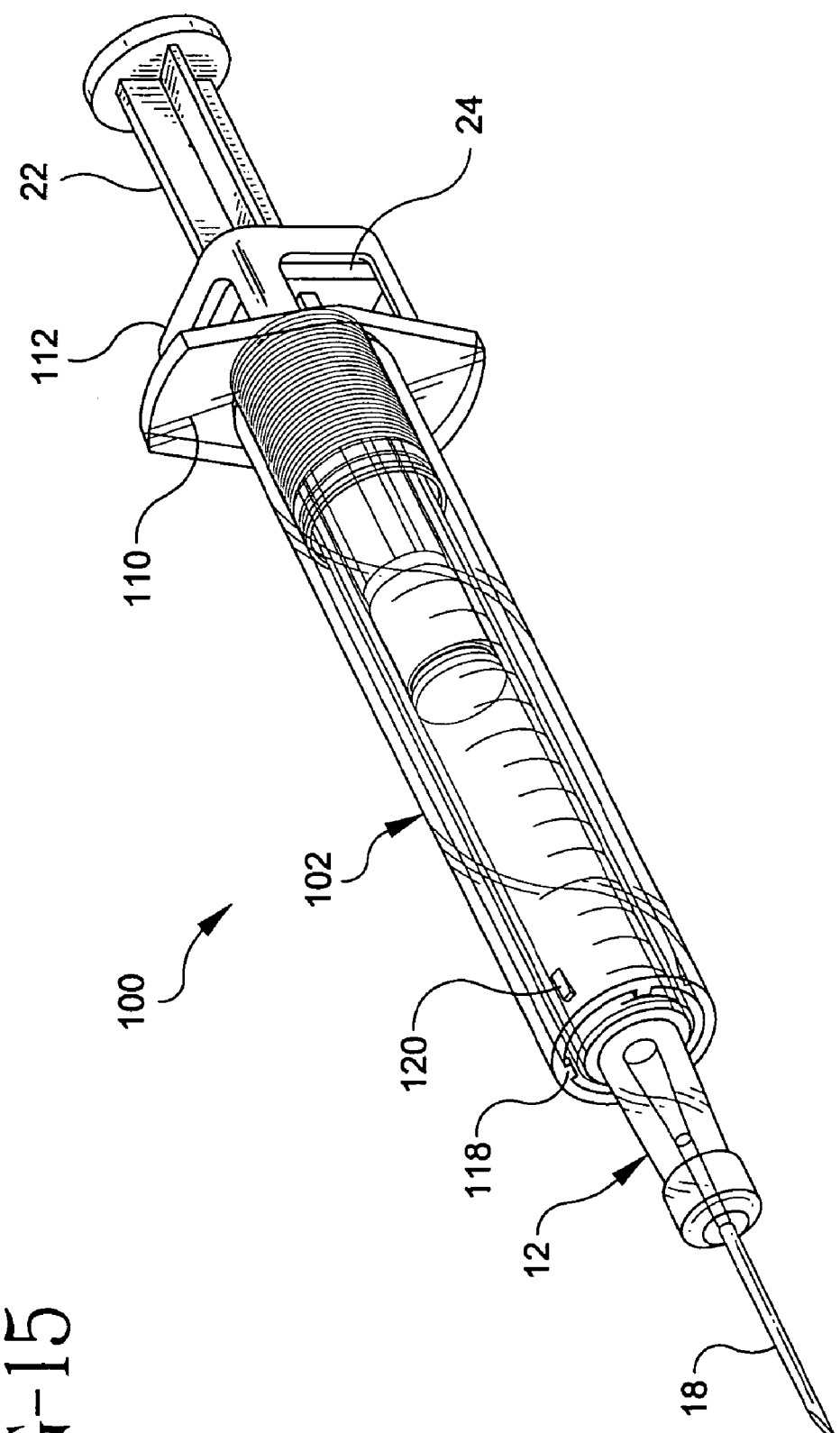
FIG. 15 is a perspective view thereof.

As shown in FIG. 14, a device 100 is provided which includes a syringe 12, a holder 102, a shield 104 and a coil spring 106. The holder 102 includes a cylindrical body 108 which defines a cylindrical enclosure for receiving the shield 104. The particular configuration of the holder is not critical so long as it is easily handled by the user of the device and accommodates the shield. A radially extending flange 110 is provided near one end of the holder. This end of the holder further includes a housing 112 for slidably retaining the flange 24 of the syringe similar to that used in the first embodiment 10 of the invention. The housing 112 includes two opposing surfaces which limit the distance the syringe flange may be moved with respect to the holder. The configuration of the housing may be modified to accommodate syringe flanges of various sizes and shapes.

Figure 16:
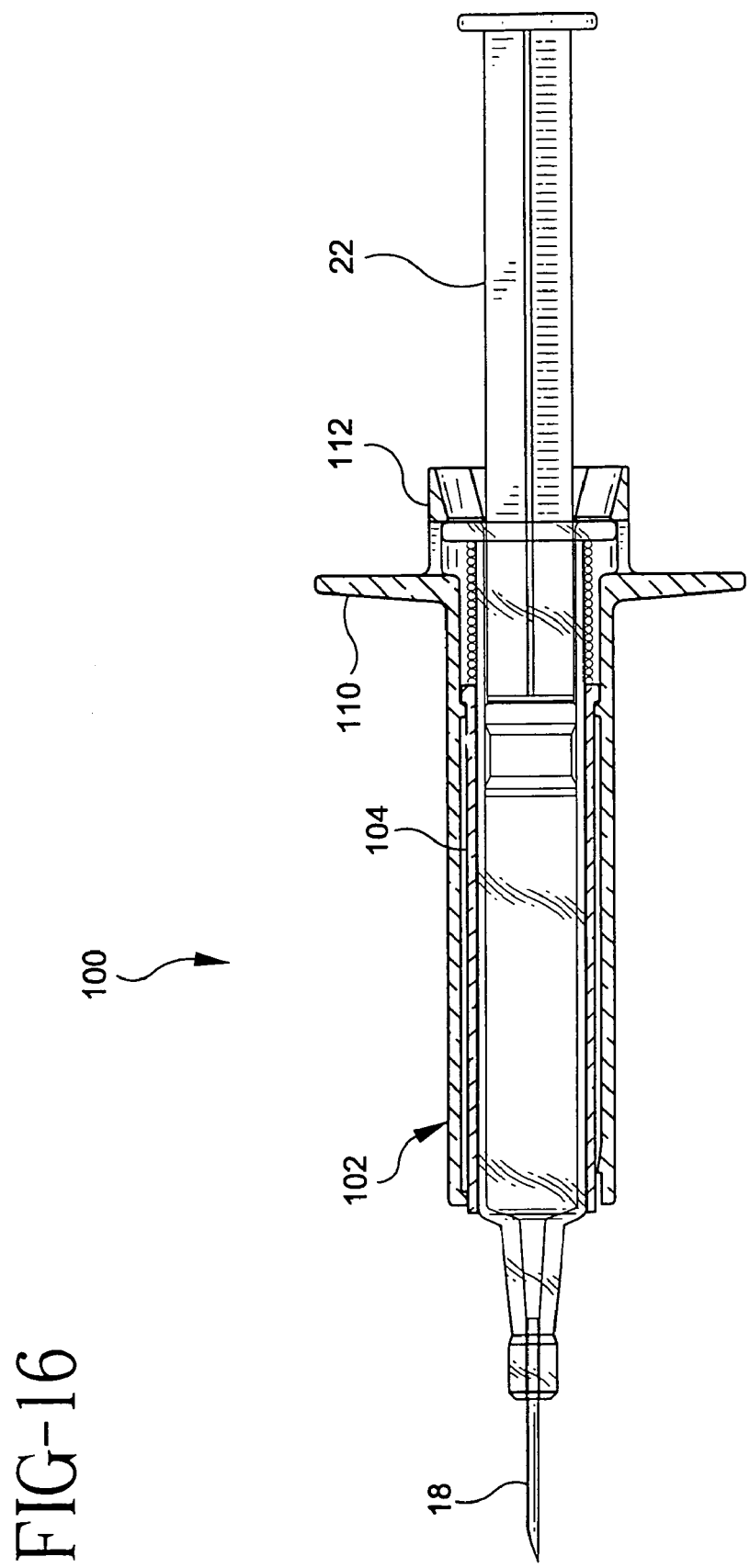
FIG. 16 is a sectional view thereof showing the device prior to actuation of the shield system thereof.

The spring 106 bears against the proximal end of the shield 104 and the distally facing surface of the syringe flange 24. The proximal end of the shield is radially enlarged, forming a collar 114. An annular stop member 116 is formed on the inner surface of the holder, and engages the collar 114 prior to use of the syringe. FIG. 16 shows the engagement of these structures. The coils of the spring are in substantially abutting relation when the syringe is in the position shown in this Figure.

The distal end of the holder includes at least a first set of detents 118 for preventing the shield 104 from being uncoupled from the holder once the collar 114 has been moved past the stop member 116. These detents are comprised of radially inwardly extending projections which are engageable with the collar 114. While the spring maintains the shield in the protective position over the needle 18, it is preferable to permanently maintain the shield in this position. A set of wedge-shaped detents 120 is accordingly provided on the inner surface of the holder. The second set of detents does not impede the passage of the collar 114 as the spring expands, but prevents retraction of the shield as the collar abuts the shoulder portions of the detents. One or both of the holder and shield preferably includes a degree of resiliency to facilitate operation of the detents as well as the collar and stop member.

Figure 17:
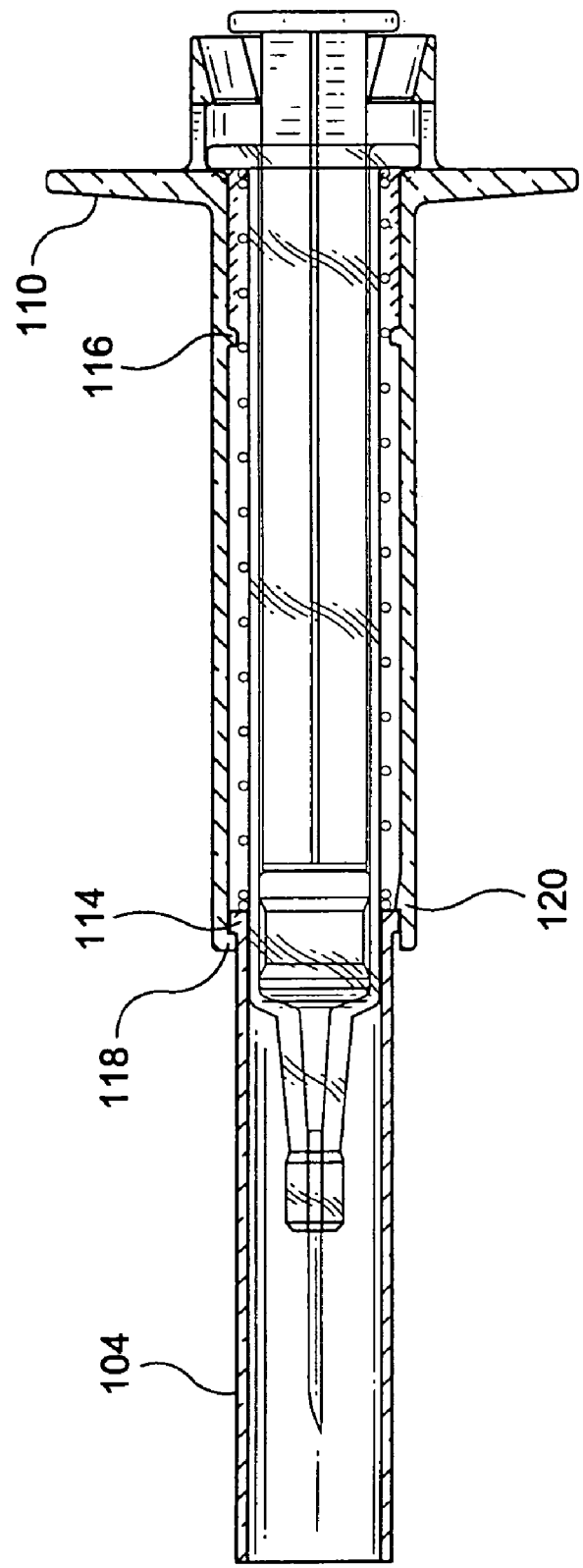
FIG. 17 is a sectional view showing the device following actuation of the shield system.
Figure 18:
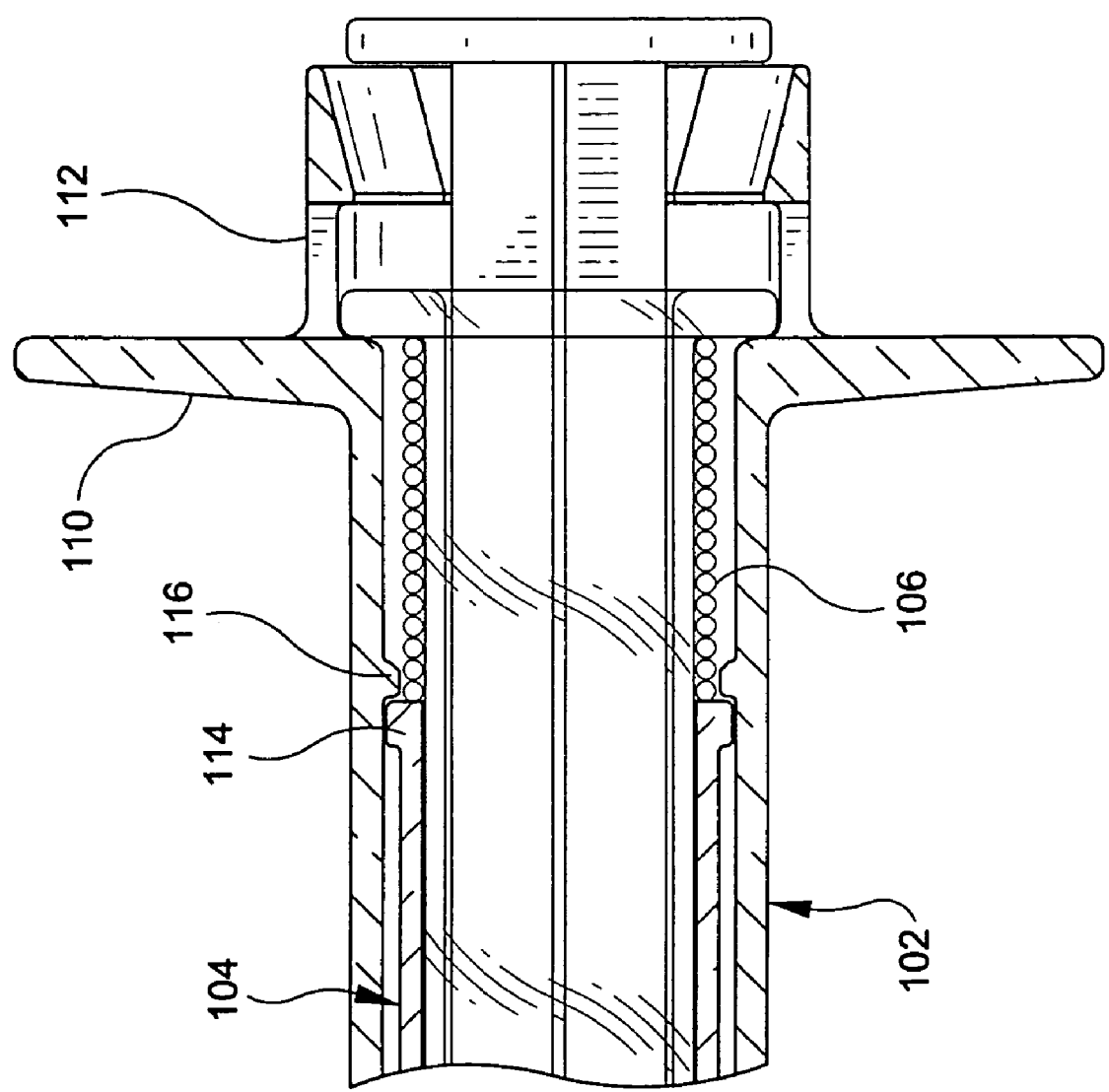
FIG. 18 is an enlarged sectional view of the proximal portion thereof immediately following actuation of the shield system.
Figure 19:
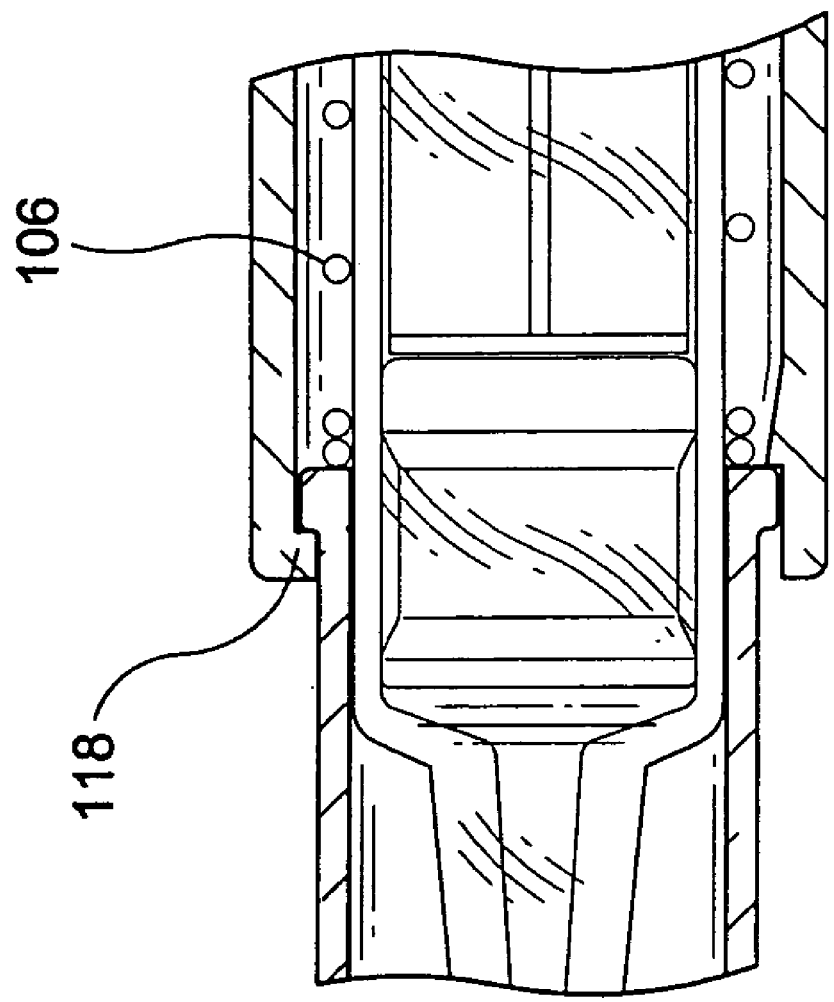
FIG. 19 is an enlarged sectional view showing a portion of the device following actuation of the shield system.

In operation, the device 100 is employed in substantially the same manner as a conventional syringe, starting with the arrangement of elements shown in FIG. 16. The user pushes the plunger rod using his thumb while the flanges of the holder are engaged by the index and middle fingers of the same hand. Once the piston has been moved to an abutting position with the end of the syringe barrel, further pressure on the plunger rod causes axial movement of the syringe itself. Due to the abutting relation of the coils of the spring to each other, the spring in effect forms a solid connection between the syringe flange and the proximal end of the shield. Axial movement of the syringe accordingly causes corresponding axial movement of the shield until the collar 114 moves beyond the stop member 116, as shown in FIG. 18. Expansion of the spring causes the shield to move to an extended position, as shown in FIG. 17.

Referring next to FIGS. 20-23, an alternate embodiment of the present invention is depicted and will now be described in detail. A medical device 200 comprising a safety shield system 214 and a syringe 216 is depicted and will now be described in detail. The safety shield system 214 depicted in FIGS. 20a-b is substantially the same as the previously described embodiments, depicted in FIGS. 1-19. However, certain differences exist between the embodiments—those difference being discussed in detail below. Where the embodiments depicted in FIGS. 20-23 are substantially the same as the embodiments depicted in FIGS. 1-19, the previous description of the inventive safety shield system will also apply to the embodiments of FIGS. 20-23.

Figure 22:
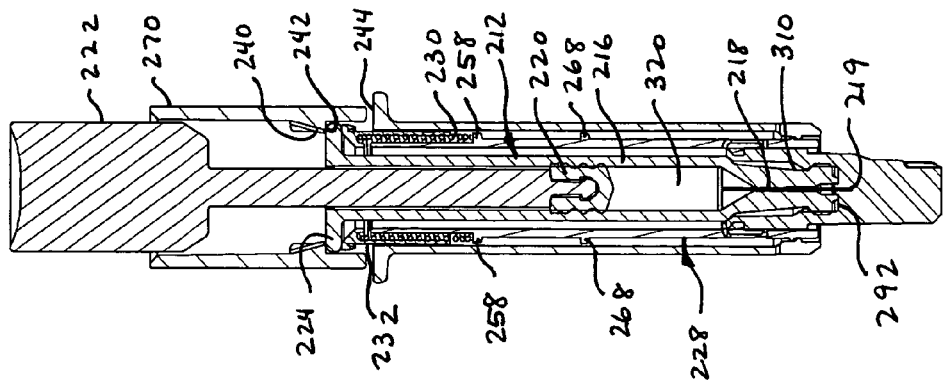
FIG. 22 is a cross-sectional side-view of the medical device depicted in FIG. 21.

With reference next to FIG. 22, the inventive safety shield system 214 is shown in cross-sectional side-view. The safety shield system 214 comprises a holder 226 and shield 228 interconnected together for selective slideable movement of the shield 228 with respect to the holder 226. The shield 228 is movable from a retracted position, depicted in FIGS. 21 and 22, in which the forward tip 219 of the needle 218 is exposed, to an extended position, depicted in FIG. 20c, in which the forward tip 219 of the needle 218 is contained within the shield 228. Movement of the shield 228 from the retracted position to the extended position is effected by disengagement of complementary structure provided on each of the holder 226 and shield 228, and further under the encouragement of a spring 230.

Figure 21:
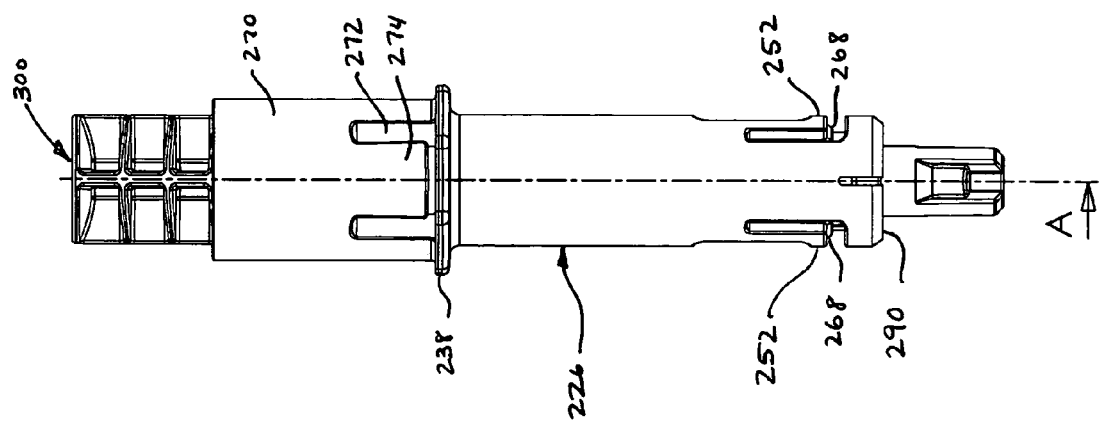
FIG. 21 is a side-view of the medical device depicted in FIGS. 20a-b.

The syringe 212 depicted in FIGS. 20, 21 and 22 differs from the syringe depicted in FIGS. 1-19 in two significant ways. First, the plunger rod 222 has a thumb pad 300 comprised of a plurality of discs 302 traversed by two intersecting walls 304, 306. The second significant difference is the length of the configuration of the hub 310 of the syringe body 216, and the length of the needle 218. The hub 310 has a generally flat skin engaging surface 292 unitarily defined thereon. The generally flat skin engaging surface 292 provides a surface to contact the patient's skin during injection. The forward tip 219 of the needle 218 is located a predetermined distance from the skin engaging surface 292, preferably ranging from 0.5 mm to 3 mm. Such a configuration limits the depth of injection of the needle 218 to the intradermal region of the patient's skin. The skin engaging surface 292 and axis of the needle 218 may be arranged generally in perpendicular relation to each other.

As depicted in FIG. 22, and from a user's perspective (i.e., that of a health care provider), the location of the finger flange 238 on the holder 226 will cause the shield 228 to move with respect to the holder 226 and with respect to the user, as discussed in more detail below. Such a configuration and orientation is preferred for embodiments of the present invention because of the selective placement of the finger flange 238 on the holder 226. That selective placement facilitates movement of the shield 228 with respect to the holder 226, while the user maintains hold of the holder 226 after completion of an injection. Alternatively, the finger flange 238 may be constructed in such a way that the holder 226 moves with respect to the shield 228 after completion of an injection.

Figure 3:
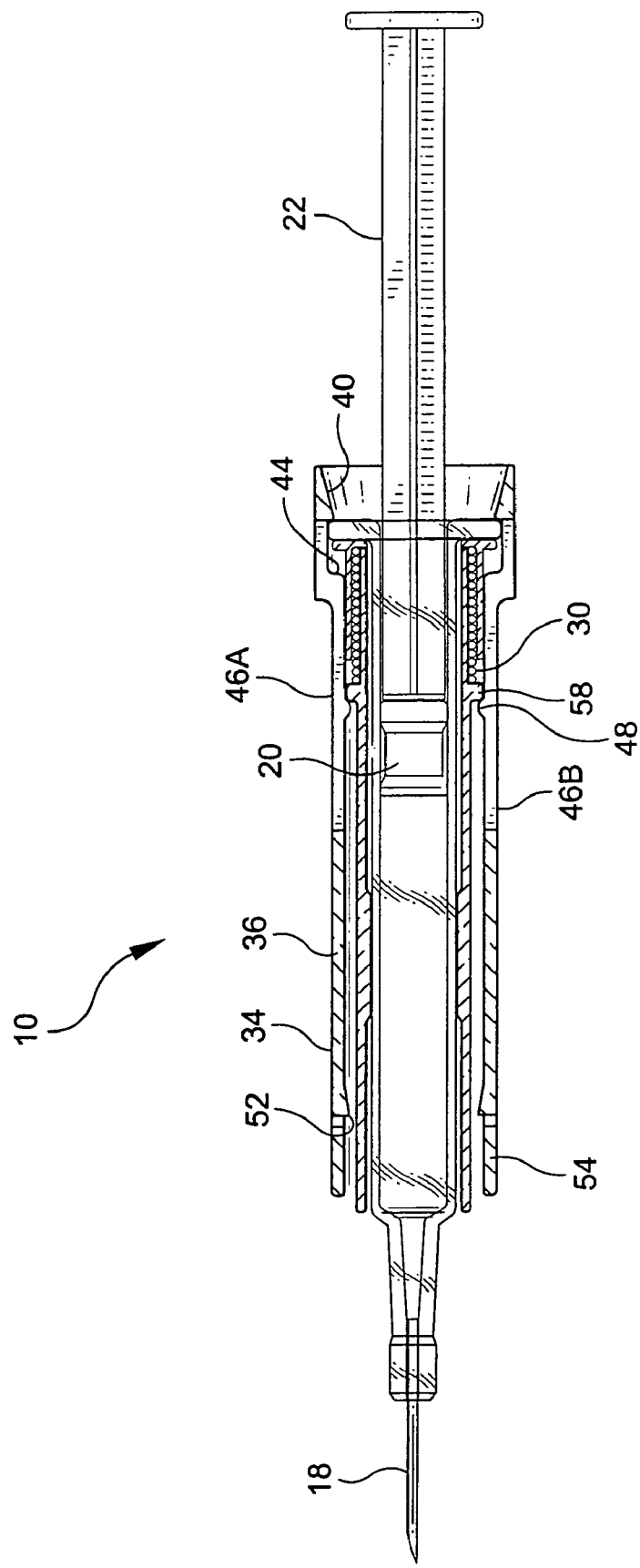
FIG. 3 is a sectional elevation view thereof.

When the shield 228 is in the retracted position, as depicted in FIG. 22, the spring 230 is in a compressed state, biasing the shield 228 toward the extended position. As noted above, complementary structure provided on each of the holder 226 and shield 228 releasably secure the shield 228 in the retracted position. An illustrative, non-limiting example of such complementary structure is depicted in FIG. 3, and designated by reference characters 48, 248 (not shown in FIG. 22) and 58, 258. In that embodiment, a generally annular stop member 48 is provided on the holder 26 in the form of an inwardly extending protrusion. Alternatively, a series of discrete protrusions (not shown) may be employed. A stop member 58, 258 in the form of a radially outwardly extending collar is provided on the shield 28, 228. This stop member 58, 258 may have a surface which is engageable with a surface of the stop member 48, 248 on the holder 26, 226. Such engagement is sufficient to prevent release of stop members 48, 248 and 58, 258 under urging of the spring 30, 230. Release of stop members 48, 248 and 58, 258 occurs upon sufficient axial movement of the syringe 12, 212, as described in more detail below. Only then may the shield 28, 228 be caused by the spring 30, 230 to move from the retracted position to the extended position. On its own, the spring 30, 230 is not able to overcome the releasable locking relation between stop members 48, 248 and 58, 258. The stop members disclosed in FIG. 3 and discussed above are illustrative examples of one embodiment of the present invention. Alternative complementary structure may be provided on the holder 226 and shield 228 to perform the desired and described releasable securing functionally of the stop members. For example, an annular stop member, similar to that depicted in FIG. 3, may be provided anywhere on the shield (i.e., at or near either end, in the middle, etc.), provided that it can releasably engage a complementary structure defined in or on the holder 226.

A syringe 212 is secured in the holder 226 by a retainer defined in a top portion of the holder 226. The top portion of the holder 226 comprises a generally continuous cylindrical wall 270, that may have one or more openings 272 defined therein. The one or more openings permit movement of a tab 274 when the syringe 212 is inserted into the holder 226. Defined on an inner surface of the wall 270 is a detent 240 that may be a continuous or an interrupted annular structure. The detent 240 is sized and shaped to permit a flange 224 of a syringe 212 to pass thereover when the syringe 212 is inserted into the holder 226, and to prevent passage of the flange 224 thereover when removal of the syringe 212 from the holder 226 is attempted. An undercut surface 242 of the detent 240 provides a surface upon which the flange 224 of the syringe 212 may rest. The flange 224 is caused to move away from the undercut surface 242 when the syringe 212 is caused to move axially in the holder 226 (as described on more detail herein). An abutment surface 244 is defined in the holder 226 in confrontingly opposite relation to the undercut surface 242. The abutment surface 244 provides a surface to arrest axial movement of the syringe 212 within the holder 226—the distance between the undercut surface 242 and abutment surface 244 defining the limit of axial movement of the syringe 212 within the holder 226—that limit being sufficient to cause disengagement of stop members 248, 258.

Such sufficient axial movement of the syringe 212 is effected at or near the end of an injection stroke (i.e., when the piston 220 is caused to move within the reservoir 320 defined by the syringe barrel 216) and upon contacting engagement of the piston 220 with an inner bottom surface of the syringe 212 (see, e.g., FIG. 8). The plunger rod 222 and piston 220 may be caused to move along an injection stroke by a user applying pressure to the thumbpad of the plunger rod 222. At or near the end of the injection stroke, the piston 220 may contact the inner bottom surface of the syringe 212, continued pressure on the plunger rod 222 will effect axial movement of the syringe 212 within the holder 226 until stop members 248 and 258 are caused to disengage. The shield 228 is then caused by the spring 230 to move freely from the retracted position to the extended position, until the shield 228 locks in the extended position by engagement of other complementary structure provided on each of the holder 226 and shield 228. An illustrative, non-limiting example of such complementary structure is depicted in FIG. 21. There, detents 252 are provided on opposite sides of the holder 226. An annular rib 268 is defined about the shield, and axially spaced apart from the stop member 258. The shield 228 may be caused to move axially by the spring 230 until annular rib 268 passes over detents 252, at which point annular rib 268 and detents 252 lockingly secure the shield 228 in the extended position, thereby covering the forward tip 219 of the needle 218 and preventing accidental needle stick injury.

The inventive safety shield system 214 may facilitate perpendicular orientation of the syringe 212 during injection. Due to the relatively short length of the needle 218, generally perpendicular orientation between the syringe 212, i.e., needle 218, and the patient's skin ensures a more reliable injection. The generally flat skin engaging surface 292 is one way in which the present invention facilitates a perpendicular orientation. In addition, a rim 290 (see, e.g., FIG. 21) of the holder 226 may be depressed against the patient's skin during an injection to stabilize the syringe 212 and facilitate a perpendicular orientation between the syringe 212 and patient's skin. The rim 290 may also limit the needle tip pressure on the skin during an intradermal injection, and may act to limit the injection depth of the needle 218. In this case, the rim 290 may provide all or part of the skin engaging surface.

Figure 23:
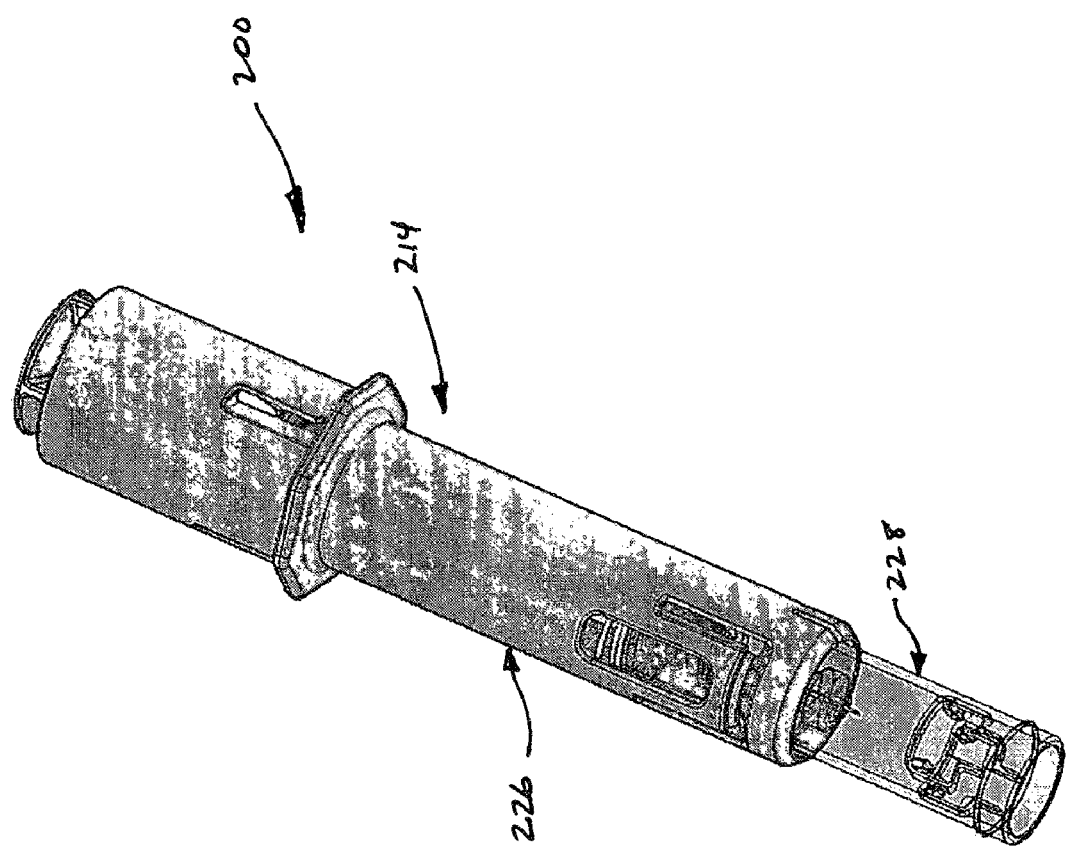
FIG. 23 is a perspective view of an alternative embodiment of a medical device in accordance with the present invention.

Referring next to FIG. 23, another alternative embodiment of the present invention is depicted. In that embodiment, the shield 228 is initially deployed in an extended position (i.e., covering the forward tip 219 of the needle 218). Due to the biasing force of the spring 230 (not shown), a user of the medical device 200 must exert pressure sufficient to overcome the spring 230 biasing force. That pressure may facilitate initial pricking of the patient's skin by way of a relatively quick injection movement, enabling a better pricking of the skin and insertion of the needle 218 into the injection site.

In this embodiment, the shield 228 may be cam-shaped, so that during an injection, the shield 228 will contact the patient's skin prior to injection and be caused to move from the extended position toward the retracted position. Upon completion of the injection, and upon removal of the needle 218 from the patient's skin, the spring 230 will cause the shield 228 to move again to the extended position thereby covering the forward tip 219 of the needle 218 and locking in place in the extended position.

It will be appreciated and understood by those skilled in the art that further and additional revisions to the invention may be devised without departing from the spirit and scope of the appended claims, the invention not being limited to the specific embodiments shown.

What is claimed is:

1. A safety shield system for use with a syringe having a barrel defining a reservoir within which a medicament may be held, the syringe having a needle affixed to the barrel and in fluid communication with the reservoir, the syringe further including a plunger rod and piston selectively movable within the reservoir along an injection stroke, the medicament being expelled from the reservoir through the needle by movement of the plunger rod and piston in the reservoir, said safety shield system comprising:
  a holder;
  a retainer defined on said holder and comprising a detent and at least one engaging pawl, said retainer securing a flange of the syringe barrel within said holder and permitting axial movement of the barrel therein and with respect thereto, the axial movement of the barrel being caused by movement of the plunger rod and piston within the reservoir;
  a shield slidably engaged to said holder, said shield being axially movable with respect to said holder from a retracted position, in which a part of the needle is not surrounded by said shield, and an extended position, in which the needle is surrounded by said shield;
  a spring urging said shield towards said extended position;
  a first stop member provided on one of said shield and said holder; and
  a second stop member provided on said other one of said shield and said holder and engageable with said first stop member to hold said shield in said retracted position;
  said barrel being capable of biasing said shield toward the needle such that sufficient axial movement of said barrel in the direction of the needle causes disengagement of said first and second stop members, allowing said spring to move said shield to the extended position.

2. A safety shield system as described in claim 1, wherein first stop member extends radially outwardly from said shield.

3. A safety shield system as described in claim 2, wherein said second stop member extends radially inwardly from said holder.

4. A safety shield system as described in claim 1, further comprising an end fitting slidably mounted to said holder and engaging an end of the syringe.

5. A safety shield system as described in claim 4, wherein the flange of the barrel engages said end fitting.

6. A safety shield system as described in claim 1, wherein said shield is positioned at least partially within said holder, said holder comprising an elongate, generally cylindrical body including a first detent and a second detent, said second detent being axially spaced from said first detent, said shield including a third detent positionable between said first and second detents when said shield is in the extended position.

7. A safety shield system as described in claim 6, wherein said second detent is radially deflectable with respect to said holder.

8. A safety shield system as described in claim 4 wherein said barrel biases said shield toward said needle through at least one intermediate component, said intermediate component is said end fitting.

9. A safety shield system as described in claim 8 wherein said barrel biases said shield toward said needle through a portion of said spring.

10. A medical device comprising:
  a syringe comprising:
    a barrel defining a reservoir within which a medicament may be held;
    a hub at an end of said barrel and defining a skin engaging surface;
    a needle having a forward tip and being in fluid communication with said reservoir, said forward tip of said needle extending beyond said skin engaging surface a distance ranging from 0.5 mm to 3 mm;
    a plunger rod having a piston secured thereto, said piston being selectively movable within said reservoir along an injection stroke, the medicament being expelled from said reservoir through said needle by movement of said piston in the reservoir; and
  a safety shield system comprising:
    a holder;
    a retainer defined on said holder and comprising a detent and at least one pawl, said retainer securing a flange of the syringe barrel within said holder and permitting axial movement of the barrel therein and with respect thereto, the axial movement of the barrel being caused by movement of the plunger rod and piston within the reservoir;
    a shield coupled to said holder, said shield being axially movable with respect to said holder from a retracted position, in which a part of the needle is not surrounded by said shield, and an extended position, in which the needle is surrounded by said shield;
    a spring urging said shield towards said extended position;
    a first stop member provided on one of said shield and said holder; and
    a second stop member provided on said other one of said shield and said holder and engageable with said first stop member to releasably hold said shield in said retracted position;
    said barrel capable of biasing said shield such that sufficient axial movement of said barrel in the direction of the needle causes disengagement of said first and second stop members, allowing said spring to move said shield to the extended position.

11. A medical device as described in claim 10, wherein first stop member extends radially outwardly from said shield.

12. A medical device as described in claim 11, wherein said second stop member extends radially inwardly from said holder.

13. A medical device as described in claim 10, further comprising an end fitting slidably mounted to said holder and engaging an end of the syringe.

14. A medical device as described in claim 13, wherein the flange of the barrel engages said end fitting.

15. A medical device as described in claim 10, wherein said shield is positioned at least partially within said holder, said holder comprising an elongate, generally cylindrical body including a first detent and a second detent, said second detent being axially spaced from said first detent, said shield including a third detent positionable between said first and second detents when said shield is in the extended position.

16. A medical device as described in claim 15, wherein said second detent is radially deflectable with respect to said holder.

17. A medical device as described in claim 13 wherein said barrel biases said shield toward said needle through at least one intermediate component, and said intermediate component is said end fitting.

18. A medical device as described in claim 17 wherein said barrel biases said shield toward said needle through a portion of said spring.

* * * * *